United States Patent
Chen et al.

(10) Patent No.: US 8,906,656 B2
(45) Date of Patent: Dec. 9, 2014

(54) COW RUMEN XYLOSE ISOMERASES ACTIVE IN YEAST CELLS

(71) Applicant: E I du Pont de Nemours and Company, Wilmington, DE (US)

(72) Inventors: Zhongqiang Chen, Wilmington, DE (US); Kristen J Kelly, Wilmington, DE (US); Rick W Ye, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 14/156,566

(22) Filed: Jan. 16, 2014

(65) Prior Publication Data

US 2014/0256049 A1    Sep. 11, 2014

Related U.S. Application Data

(62) Division of application No. 13/792,308, filed on Mar. 11, 2013, now Pat. No. 8,669,076.

(51) Int. Cl.
*C12N 9/90*    (2006.01)

(52) U.S. Cl.
CPC ........................................ *C12N 9/90* (2013.01)
USPC .......................................................... 435/161

(58) Field of Classification Search
CPC .............. C12N 9/90; C12N 9/92; C12N 1/18; C12N 1/20; C12N 1/22; C12N 9/001; C12N 9/1205; C12N 9/2462
See application file for complete search history.

(56) References Cited

U.S. PATENT DOCUMENTS

| | | | |
|---|---|---|---|
| 5,686,276 A | 11/1997 | Laffend et al. | |
| 6,013,494 A | 1/2000 | Nakamura et al. | |
| 6,514,733 B1 | 2/2003 | Emptage et al. | |
| 7,005,291 B1 | 2/2006 | Nair et al. | |
| 7,622,284 B2 | 11/2009 | Op Den Camp et al. | |
| 7,629,151 B2 | 12/2009 | Gold et al. | |
| 7,851,188 B2 | 12/2010 | Donaldson et al. | |
| 7,943,366 B2 | 5/2011 | Rajgarhia et al. | |
| 8,058,040 B2 | 11/2011 | Op Den Camp et al. | |
| 8,093,037 B2 | 1/2012 | Picataggio et al. | |
| 8,114,974 B2 | 2/2012 | Picataggio et al. | |
| 8,129,171 B2 | 3/2012 | Boles et al. | |
| 8,206,970 B2 | 6/2012 | Eliot et al. | |
| 2006/0216804 A1 | 9/2006 | Karhumaa | |
| 2007/0155000 A1 | 7/2007 | Nilsson et al. | |
| 2007/0292927 A1 | 12/2007 | Donaldson et al. | |
| 2008/0182308 A1 | 7/2008 | Donaldson et al. | |
| 2009/0061502 A1 | 3/2009 | Nilsson et al. | |
| 2009/0155870 A1 | 6/2009 | Donaldson et al. | |
| 2010/0028975 A1 | 2/2010 | Gorwa-Grauslund | |
| 2010/0112658 A1 | 5/2010 | Hughes et al. | |
| 2011/0318801 A1 | 12/2011 | Kahsay et al. | |
| 2012/0184020 A1 | 7/2012 | Picataggio et al. | |
| 2012/0225452 A1 | 9/2012 | Bao et al. | |

FOREIGN PATENT DOCUMENTS

| | | |
|---|---|---|
| WO | 2006115455 A1 | 11/2006 |
| WO | 2011078262 A1 | 6/2011 |
| WO | 2011079388 A1 | 7/2011 |
| WO | 2011149353 A1 | 12/2011 |
| WO | 2011153516 A2 | 12/2011 |
| WO | 2012009272 A2 | 1/2012 |
| WO | 2013003219 A1 | 1/2013 |
| WO | 2014018552 A1 | 1/2014 |

OTHER PUBLICATIONS

GenBank Accession No. ZP_04453767, Nov. 27, 2012.
U.S. Appl. No. 13/792321, filed Mar. 11, 2013.
U.S. Appl. No. 13/792668, filed Mar. 11, 2013.
Matsushika, Akinori et al., Ethanol production from xylose in engineered *Saccharomyces cerevisiae* strains: current state and perspectives, Applied Microbiology and Biotechnology, 2009, pp. 37-53, vol. 84.
Kuyper, Marko et al., Metabolic engineering of a xylose-isomerase-expressing *Saccharomyces cerevisiae* strain for rapid anaerobic xylose fermentation, FEMS Yeast Research, 2005, pp. 399-409, vol. 5.
Hector, Ronald E et al., Growth and fermentation of D-xylose by *Saccharomyces cerevisiae* expressing a novel D-xylose isomerase originating from the bacterium *Prevotella ruminicola* TC2-24, Biotechnology for Biofuels, May 2013, pp. 84 (12 pp.), vol. 6, No. 1.
International Search Report dated Jul. 7, 2014, International Application No. PCT/2014/022267.

*Primary Examiner* — Tekchand Saidha
*Assistant Examiner* — Rama P Ramanujam

(57)    ABSTRACT

Polypeptides were identified among translated coding sequences from a metagenomic cow rumen database, that were shown to provide xylose isomerase activity in yeast cells. The xylose isomerase activity can complete a xylose utilization pathway so that yeast can use xylose in fermentation, such as xylose in biomass hydrolysate.

6 Claims, No Drawings

COW RUMEN XYLOSE ISOMERASES ACTIVE IN YEAST CELLS

FIELD OF THE INVENTION

The invention relates to the field of genetic engineering of yeast. More specifically, a group of xylose isomerases are identified that are active in yeast cells engineered for their expression.

BACKGROUND OF THE INVENTION

Currently fermentative production of ethanol is typically by yeasts, particularly *Saccharomyces cerevisiae*, using hexoses obtained from grains or mash as the carbohydrate source. Use of hydrolysate prepared from cellulosic biomass as a carbohydrate source for fermentation is desirable, as this is a readily renewable resource that does not compete with the food supply. After glucose, the second most abundant sugar in cellulosic biomass is xylose, a pentose. *Saccharomyces cerevisiae* is not naturally capable of metabolizing xylose, but can be engineered to metabolize xylose with expression of xylose isomerase activity to convert xylose to xylulose, and additional pathway engineering.

Success in expressing heterologous xylose isomerase enzymes, and particularly those that are derived from bacterial sources, that are active in yeast has been limited. Some specific bacterial xylose isomerase sequences have been reported to provide xylose isomerase activity for a xylose utilization pathway in yeast. For example U.S. Pat. No. 7,622,284 discloses a yeast cell expressing a xylose isomerase isolated from *Piromyces* sp. that is able to use xylose as a substrate. US 2012/0184020 discloses eukaryotic cells expressing a xylose isomerase isloated from *Ruminococcus flavefaciens*. WO2011078262 discloses several xylose isomerases from each of *Reticulitermes speratus* and *Mastotermes darwiniensis* and proteins with high sequence identities to these, and their expression in eukaryotic cells. WO212009272 discloses constructs and fungal cells containing a xylose isomerase from *Abiotrophia defectiva*.

There remains a need for additional engineered yeast cells that express xylose isomerase activity for successful utilization of xylose, thereby allowing effective use of sugars obtained from cellulosic biomass during fermentation.

SUMMARY OF THE INVENTION

The invention provides recombinant yeast cells that are engineered to express a polypeptide having xylose isomerase activity.

Accordingly, the invention provides a recombinant yeast cell comprising a heterologous nucleic acid molecule encoding a polypeptide having xylose isomerase activity and amino acid sequence having greater than 85% sequence identity to the amino acid sequence of SEQ ID NO:1, or greater than 86% sequence identity to the amino acid sequence of SEQ ID NO:3, wherein the polypeptide has xylose isomerase activity in the yeast cell.

In another aspect, the invention provides a method for producing a yeast cell that has xylose isomerase activity comprising:
 a) providing a yeast cell;
 b) introducing a heterologous nucleic acid molecule encoding a polypeptide having xylose isomerase activity and amino acid sequence with at least 85% sequence identity to the amino acid sequence of SEQ ID NO:1, or greater than 86% seqeunce identity to the amino acid seqeunced of SEQ ID NO:3,
 wherein a yeast cell having xylose isomerase activity is produced.

SEQUENCE DESCRIPTIONS

The invention can be more fully understood from the following detailed description and the accompanying sequence descriptions which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

SEQ ID NOs for xylose isomerase polypeptides, and coding regions that are codon optimized for expression in *S. cerevisiae*

| Identification | SEQ ID NO: amino acid | SEQ ID NO: nucleotide codon opt. |
|---|---|---|
| Ru4 | 1 | 2 |
| Ru1 | 3 | 4 |
| Ru2 | 5 | 6 |
| Ru3 | 7 | 8 |
| *Ruminococcus champanellensis* 18P13 | 9 | 10 |
| *Ruminococcus flavefaciens* FD-1 | 11 | *nd |
| *Abiotrophis defectiva* | 12 | *nd |

*nd = not designed

SEQ ID NO:13 is the nucleotide sequence of the pHR81 vector containing the ILVp-xylA(Ru2)-ILV5t chimeric gene.

SEQ ID NO:14 is the nucleotide sequence of P5 Integration Vector.

SEQ ID NO:15 is the nucleotide sequence of a URA3 deletion scar.

SEQ ID NO:16 is the nucleotide sequence of the upstream ura3Δ post deletion region.

SEQ ID NO:17 is the nucleotide sequence of the downstream ura3Δ post deletion region.

SEQ ID NO:18 is the nucleotide sequence of the upstream his3Δ post deletion region.

SEQ ID NO:19 is the nucleotide sequence of the downstream his3Δ post deletion region.

SEQ ID NO:20 is the nucleotide sequence of pJT254.

DETAILED DESCRIPTION

The following definitions may be used for the interpretation of the claims and specification:

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "xylose isomerase" refers to an enzyme that catalyzes the interconversion of D-xylose and D-xylulose. Xylose isomerases (XI) belong to the group of enzymes classified as EC 5.3.1.5.

The term "xylose utilization pathway" refers to a metabolic pathway comprising genes encoding enzymes sufficient to convert xylose to a target chemical. In the situation where the target chemical is ethanol such a pathway typically comprises genes encoding the following enzymes: xylulokinase (XKS1), transaldolase (TAL1), transketolase 1 (TKL1), D-ribulose-5-phosphate 3-epimerase (RPE1), and ribose 5-phosphate ketol-isomerase (RKI1). Elements of this pathway may be native or heterologous to the host cell.

The term "gene" refers to a nucleic acid fragment that expresses a specific protein or functional RNA molecule, which may optionally include regulatory sequences preceding (5' non-coding sequences) and following (3' non-coding sequences) the coding sequence. "Native gene" or "wild type gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

The term "promoter" or "Initiation control regions" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters".

The term "expression", as used herein, refers to the transcription and stable accumulation of coding (mRNA) or functional RNA derived from a gene. Expression may also refer to translation of mRNA into a polypeptide. "Overexpression" refers to the production of a gene product in transgenic organisms that exceeds levels of production in normal or non-transformed organisms.

The term "transformation" as used herein, refers to the transfer of a nucleic acid fragment into a host organism, resulting in genetically stable inheritance. The transferred nucleic acid may be in the form of a plasmid maintained in the host cell, or some transferred nucleic acid may be integrated into the genome of the host cell. Host organisms containing the transformed nucleic acid fragments are referred to as "transgenic" or "recombinant" or "transformed" organisms.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "selectable marker" means an identifying factor, usually an antibiotic or chemical resistance gene, that is able to be selected for based upon the marker gene's effect, i.e., resistance to an antibiotic, wherein the effect is used to track the inheritance of a nucleic acid of interest and/or to identify a cell or organism that has inherited the nucleic acid of interest.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

The term "carbon substrate" or "fermentable carbon substrate" refers to a carbon source capable of being metabolized by microorganisms. A type of carbon substrate is "fermentable sugars" which refers to oligosaccharides and monosaccharides that can be used as a carbon source by a microorganism in a fermentation process.

The term "lignocellulosic" refers to a composition comprising both lignin and cellulose. Lignocellulosic material may also comprise hemicellulose.

The term "cellulosic" refers to a composition comprising cellulose and additional components, which may include hemicellulose and lignin.

The term "saccharification" refers to the production of fermentable sugars from polysaccharides.

The term "pretreated biomass" means biomass that has been subjected to thermal, physical and/or chemical pretreatment to increase the availability of polysaccharides in the biomass to saccharification enzymes.

"Biomass" refers to any cellulosic or lignocellulosic material and includes materials comprising cellulose, and optionally further comprising hemicellulose, lignin, starch, oligosaccharides and/or monosaccharides.

Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn cobs, crop residues such as corn husks, corn stover, corn grain fiber, grasses, beet pulp, wheat straw, wheat chaff, oat straw, barley straw, barley hulls, hay, rice straw, rice hulls, switchgrass, miscanthus, cord grass, reed canary grass, waste paper, sugar cane bagasse, sorghum bagasse, sorghum stover, soybean stover, components obtained from milling of grains, trees, branches, roots, leaves, wood chips, sawdust, palm waste, shrubs and bushes, vegetables, fruits, flowers, and animal manure.

"Biomass hydrolysate" refers to the product resulting from saccharification of biomass. The biomass may also be pretreated or pre-processed prior to saccharification.

The term "heterologous" means not naturally found in the location of interest. For example, a heterologous gene refers to a gene that is not naturally found in the host organism, but that is introduced into the host organism by gene transfer. For example, a heterologous nucleic acid molecule that is present in a chimeric gene is a nucleic acid molecule that is not naturally found associated with the other segments of the chimeric gene, such as the nucleic acid molecules having the coding region and promoter segments not naturally being associated with each other.

As used herein, an "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign program of the LASERGENE bioinformatics computing suite (DNASTAR Inc., Madison, Wis.).

Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS.* 5:151-153 (1989); Higgins, D. G. et al., *Comput. Appl. Biosci.,* 8:189-191 (1992)) and found in the MegAlign v8.0 program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191(1992); Thompson, J. D. et al, Nucleic Acid Research, 22 (22): 4673-4680, 1994) and found in the MegAlign v8.0 program of the LASERGENE bioinformatics computing suite (DNASTAR Inc.). Default parameters for multiple alignment (stated as protein/nucleic acid (GAP PENALTY=10/15, GAP LENGTH PENALTY=0.2/6.66, Delay Divergen Seqs(%)=30/30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program. Sequence identities referred to herein shall always be considered to have been determined according to the parameters set forth above unless otherwise noted.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., J. Mol. Biol., 215:403-410 (1990)); 3.) DNASTAR (DNASTAR, Inc. Madison, Wis.); 4.) Sequencher (Gene Codes Corporation, Ann Arbor, Mich.);

and 5.) the FASTA program incorporating the Smith-Waterman algorithm (W. R. Pearson, Comput. Methods Genome Res., [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The term "target compound" or "target chemical" refers to a compound made by a microorganism via an endogenous or recombinant biosynthetic pathway which is able to metabolize a fermentable carbon source to produce the target compound.

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et. al., *Short Protocols in Molecular Biology*, 5$^{th}$ Ed. Current Protocols, John Wiley and Sons, Inc., N.Y., 2002. Additional methods used here are in *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.).

The present invention relates to engineered yeast strains that have xylose isomerase enzyme activity. A challenge for engineering yeast to utilize xylose, which is the second most predominant sugar obtained from cellulosic biomass, is to produce sufficient xylose isomerase activity in the yeast cell. Xylose isomerase catalyzes the conversion of xylose to xylulose, which is the first step in a xylose utilization pathway. Applicants have found that expression of specific xylose isomerase polypeptides provides xylose isomerase activity in the yeast cell, while expression of other xylose isomerase polypeptides does not provide activity. A yeast cell expressing xylose isomerase activity provides a host cell for expression of a complete xylose utilization pathway, thereby engineering a yeast cell that can produce a target compound, such as ethanol, butanol, or 1,3-propanediol, using xylose derived from lignocellulosic biomass as a carbon source.

Yeast Host Cells

Yeast cells of the invention are those that comprise a functional bacterial xylose isomerase and a capable of the production of a target compound. Preferred target compounds are those of commercial value including but not limited to ethanol, butanol, or 1,3-propanediol.

Any yeast cells that either produce a target chemical, or can be engineered to produce a target chemical, may be used as host cells herein. Examples of such yeasts include, but are not limited to, yeasts of the genera *Kluyveromyces, Candida, Pichia, Hansenula, Schizosaccharomyces, Kloeckera, Schwammiomyces, Yarrowia*, and *Saccharomyces*.

Yeast cells of the invention comprising an active bacterial xylose isomerase may be engineered according to methods well known in the art. For example yeast cell that have the native ability to produce ethanol from C6 sugars may be transferred with genes comprising C5 metabolic pathways including the bacterial xylose isomerase of the invention. Such cells may be capable of either aerobic or anaerobic fermentive ethanol production.

In other embodiments yeast cells may be engineered to express a pathway for synthesis of butanol or 1,3-propanediol. Engineering of pathways for butanol synthesis (including isobutanol, 1-butanol, and 2-butanol) have been disclosed, for example in U.S. Pat. No. 8,206,970, US 20070292927, US 20090155870, U.S. Pat. No. 7,851,188, and US 20080182308, which are incorporated herein by reference. Engineering of pathways for 1,3-propanediol have been disclosed in U.S. Pat. No. 6,514,733, U.S. Pat. No. 5,686,276, U.S. Pat. No. 7,005,291, U.S. Pat. No. 6,013,494, and U.S. Pat. No. 7,629,151, which are incorporated herein by reference.

For utilization of xylose as a carbon source, a yeast cell is engineered for expression of a complete xylose utilization pathway. Engineering of yeast such as *S. cerevisiae* for production of ethanol from xylose is described in Matsushika et al. (Appl. Microbiol. Biotechnol. (2009) 84:37-53) and in Kuyper et al. (FEMS Yeast Res. (2005) 5:399-409). In one embodiment, in addition to engineering a yeast cell as disclosed herein to have xylose isomerase activity, the activities of other pathway enzymes are increased in the cell to provide the ability to grow on xylose as a sole carbon source. Typically the activity levels of five pentose pathway enzymes are increased: xylulokinase (XKS1), transaldolase (TAL1), transketolase 1 (TKL1), D-ribulose-5-phosphate 3-epimerase (RPE1), and ribose 5-phosphate ketol-isomerase (RKI1). Any method known to one skilled in the art for increasing expression of a gene may be used. For example, as described herein in Example 1, these activities may be increased by expressing the host coding region for each protein using a highly active promoter. Chimeric genes for expression are constructed and are integrated into the yeast genome. Alternatively, heterologous coding regions for these enzymes may be expressed in the yeast cell to obtain increased enzyme activities. For additional methods for engineering yeast capable of metabolizing xylose see for example U.S. Pat. No. 7,622,284B2, U.S. Pat. No. 8,058,040B2, U.S. Pat. No. 7,943,366 B2, WO2011153516A2, WO2011149353A1, WO2011079388A1, US20100112658A1, US20100028975A1, US20090061502A1, US20070155000A1, WO2006115455A1, US20060216804A1 and U.S. Pat. No. 8,129,171B2.

In one embodiment the present yeast cell has xylose isomerase activity as described below, and additional genetic engineering to provide a complete xylose utilization pathway as described above. These cells are able to grow in medium containing xylose as the sole carbon source. More typically, these cells are grown in medium containing xylose as well as other sugars such as glucose and arabinose. This allows effective use of the sugars found in a hydrolysate medium that is prepared from cellulosic biomass by pretreatment and saccharification.

Xylose Isomerase

Expression of xylose isomerases in yeast cells has been problematic; in particular, many bacterial xylose isomerases have been found to have little to no activity when expressed in yeast cells. In the present recombinant yeast cell, xylose isomerase activity is provided by expression of a heterologous nucleic acid molecule encoding a polypeptide having an amino acid sequence with greater than 85% sequence identity to an amino acid sequence identified among translated open reading frames of a metagenomic cow rumen database (Matthias Hess, et al. Science 331:463-467 (2011)). The identified amino acid sequence is called herein Ru4 (SEQ ID NO:1). This sequence was identified by BLAST searching using xylose isomerase sequences from *Ruminococcus flavefaciens* FD-1 (SEQ ID NO:11) and from *Ruminococcus champanel-* lensis 18P13 (SEQ ID NO:9). It is from an uncultured bacterium from cow rumen. The identities of the RU4 amino acid sequence to these two sequences are 64.1% and 67.5%, respectively (see Table 2). SEQ ID NO:11 is identical to the Ruminococcus flavefaciens xylose isomerase of SEQ ID NO:31 in US 2012/0184020.

Expression of a nucleic acid molecule encoding Ru4 in *S. cerevisiae* was found herein (Example 3) to allow growth in medium containing xylose as the sole sugar, of a *S. cerevisiae* strain containing a xylose utilization pathway but lacking xylose isomerase activity. Xylose was utilized and ethanol was produced by the yeast cells. Thus expression of Ru4 provided xylose isomerase activity to complete the xylose utilization pathway in the yeast cells. Of publicly known amino acid sequences, the one having the greatest sequence identity to Ru4 was a hypothetical protein from *Abiotrophis defectiva* ATCC 49176 (SEQ ID NO:12; Accession #ZP 04453767), with 81.5% identity. SEQ ID NO:12 is identical to SEQ ID NO:2 of WO 2102/009272, which is identified therein as *Abiotrophia defectiva* xylose isomerase. Sequence identities of Ru4 to other amino acid sequences that were known or identified herein are given in Table 2.

Any polypeptide having xylose isomerase activity and having greater than 85% sequence identity to SEQ ID NO:1 may be expressed in the present yeast cell. In various embodiments the polypeptide may have amino acid sequence identity of greater than 85%, 86%, 87%, 88%, 89%, 90%, 91%, 92%, 93%, 94%, 95%, 96%, 97%, 98%, 99% or up to 100% to SEQ ID NO:1.

An additional polypeptide having an amino acid sequence with 86.1% identity to the amino acid sequence of Ru4 was identified in the same BLAST search, and is herein called Ru1 (SEQ ID NO:3). It is also from an uncultured bacteria from cow rumen. The identities of the RU1 amino acid sequence to xylose isomerase sequences from *Ruminococcus flavefaciens* FD-1 (SEQ ID NO:11) and from *Ruminococcus champanellensis* 18P13 (SEQ ID NO:9) are 64.4% and 64.3%, respectively (see Table 2).

Expression of a nucleic acid molecule encoding Ru1 in *S. cerevisiae* was found herein (Example 3) to allow growth, xylose utilization, and ethanol production by a *S. cerevisiae* strain containing a xylose utilization pathway but lacking xylose isomerase activity, in medium containing xylose as the sole sugar. Thus expression of Ru1 provided xylose isomerase activity to complete the xylose utilization pathway in the yeast cells. Of publicly known amino acid sequences, the one having the greatest sequence identity to Ru1 was a hypothetical protein from *Abiotrophis defectiva* ATCC 49176 (SEQ ID NO:12; Accession #ZP 04453767), with 84.0% identity. SEQ ID NO:12 is identical to SEQ ID NO:2 of WO 2102/009272, which is identified therein as *Abiotrophia defectiva* xylose isomerase. Sequence identities of Ru1 to other amino acid sequences that were known or identified herein are given in Table 2.

Any polypeptide having xylose isomerase activity and having greater than 85% sequence identity to SEQ ID NO:3 may be expressed in the present yeast cell. In various embodiments the polypeptide may have amino acid sequence identity of greater than 85%, 86%, 87%, 88%, 89%, 90%, 91%, 92%, 93%, 94%, 95%, 96%, 97%, 98%, 99% or up to 100% to SEQ ID NO:3.

Thus in one embodiment a polypeptide having an amino acid sequence that has greater than 86% identity to either of SEQ ID NO:1 or SEQ ID NO:3 is expressed in the present yeast cell. In various embodiments the polypeptide may have amino acid sequence identity of about 87%, 88%, 89%, 90%, 91%, 92%, 93%, 94%, 95%, 96%, 97%, 98%, 99% or up to 100% to either of SEQ ID NO:1 or SEQ ID NO:3.

When transformed with the xylose isomerase of the invention a *S. cerevisiae* demonstrated increase growth, xylose utilization and ethanol yield when grown in xylose containing medium. Xylose isomerase proteins, having as much as 83% identity to SEQ ID NO:1, or 3 did not have the same effect, suggesting that the ability of the enzyme to be active in a yeast host may not be sequence dependent. Specifically, sequences named herein as Ru2 (SEQ ID NO:5) and Ru3 (SEQ ID NO:7) have amino acid sequence identities to Ru1 and Ru4 in the range of 75% to 83% (see Table 2). Thus sequence identity that is as high as 83% to xylose isomerases that provide activity in yeast cells is not sufficient to predict that a xylose isomerase protein will provide xylose isomerase activity in yeast cells.

TABLE 2

Comparison of xylose isomerase amino acid sequence identities

| | Ru1 | Ru2 | Ru3 | Ru4 | XI from *R. flavefaciens* | XI from *R. champanellensis* |
|---|---|---|---|---|---|---|
| Ru1 | | | | | | |
| Ru2 | 76.9 | | | | | |
| Ru3 | 83.2 | 78.4 | | | | |
| Ru4 | 86.1 | 75.3 | 80.2 | | | |
| XI from *R. flavefaciens* | 64.4 | 59.1 | 63.9 | 64.1 | | |
| XI from *R. champanellensis* | 64.3 | 59.5 | 63.0 | 67.5 | 77.4 | |
| XI from *A. defectiva* | 84.0 | 74.9 | 80.7 | 81.5 | 61.9 | 61.0 |

The present amino acid sequences are not native to yeast cells, thus their encoding nucleic acid sequences are heterologous to yeast cells. For expression, nucleic acid molecules encoding the present polypeptides may be designed using codon optimization for the desired yeast cell, as is well known to one skilled in the art. For example, for expression of Ru4 and Ru1 in *Saccharomyces cerevisiae*, nucleic acid molecules named xylA(Ru4) (SEQ ID NO:2) and xylA(Ru1) (SEQ ID NO:4) were designed using codon-optimization for expression *S. cerevisiae*.

Methods for gene expression in yeasts are known in the art (see for example *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.). Expression of genes in yeast typically requires a promoter, operably linked to the coding region of interest, and a transcriptional terminator. A number of yeast promoters can be used in constructing expression cassettes for genes encoding the desired proteins, including, but not limited to constitutive promoters FBA1, GPD1, ADH1, GPM, TPI1, TDH3, PGK1, ILV5p, and the inducible promoters GAL1, GAL10, and CUP1. Suitable transcription terminators include, but are not limited to FBAt, GPDt, GPMt, ERG10t, GAL1t, CYC1t, ADH1t, TAL1t, TKL1t, ILV5t, and ADHt.

Suitable promoters, transcriptional terminators, and coding regions may be cloned into *E. coli*-yeast shuttle vectors, and transformed into yeast cells. These vectors allow strain propagation in both *E. coli* and yeast strains.

Typically the vector contains a selectable marker and sequences allowing autonomous replication or chromosomal integration in the desired host. Typically used plasmids in yeast are shuttle vectors pRS423, pRS424, pRS425, and pRS426 (American Type Culture Collection, Rockville, Md.), which contain an *E. coli* replication origin (e.g., pMB1), a yeast 2µ origin of replication, and a marker for nutritional selection. The selection markers for these four vectors are His3 (vector pRS423), Trp1 (vector pRS424), Leu2 (vector pRS425) and Ura3 (vector pRS426). Additional vectors that may be used include pHR81 (ATCC #87541) and pRS313 (ATCC #77142). Construction of expression vectors with chimeric genes encoding the desired proteins may be performed by either standard molecular cloning techniques in *E. coli* or by the gap repair recombination method in yeast.

The gap repair cloning approach takes advantage of the highly efficient homologous recombination in yeast. Typically, a yeast vector DNA is digested (e.g., in its multiple cloning site) to create a "gap" in its sequence. The "gapped" vector and insert DNAs having sequentially overlapping ends (overlapping with each other and with the gapped vector ends, in the desired order of inserts) are then co-transformed into yeast cells which are plated on the medium containing the appropriate compound mixtures that allow complementation of the nutritional selection markers on the plasmids. The presence of correct insert combinations can be confirmed by PCR mapping using plasmid DNA prepared from the selected cells. The plasmid DNA isolated from yeast can then be transformed into an *E. coli* strain, e.g. TOP10, followed by mini preps and restriction mapping to further verify the plasmid construct. Finally the construct can be verified by sequence analysis.

Like the gap repair technique, integration into the yeast genome also takes advantage of the homologous recombination system in yeast. Typically, a cassette containing a coding region plus control elements (promoter and terminator) and auxotrophic marker is PCR-amplified with a high-fidelity DNA polymerase using primers that hybridize to the cassette and contain 40-70 base pairs of sequence homology to the regions 5' and 3' of the genomic area where insertion is desired. The PCR product is then transformed into yeast cells which are plated on medium containing the appropriate compound mixtures that allow selection for the integrated auxotrophic marker. Transformants can be verified either by colony PCR or by direct sequencing of chromosomal DNA.

The present invention provides a method for producing a yeast cell that has xylose isomerase activity following the teachings above. In one embodiment a heterologous nucleic acid molecule encoding a polypeptide having xylose isomerase activity and amino acid sequence with greater than 85% sequence identity to the amino acid sequence of SEQ ID NO:1 is introduced into a yeast strain. In various embodiments the amino acid sequence of the polypeptide has at least about 86% identity to either of SEQ ID NO:1 or SEQ ID NO:3. Further description of the amino acid sequences of the polypeptide encoded by the nucleic acid molecule that may be introduced is as disclosed above.

In one embodiment the introduced nucleic acid molecule is a part of a chimeric gene that is introduced into a yeast cell for expression, as described above.

In one embodiment the described nucleic acid molecule is introduced into a yeast cell which has other genetic modifications providing a complete xylose utilization pathway, once the xylose isomerase activity is introduced, as described above for the yeast host cell. Introduction of xylose isomerase activity and the additional genetic modifications may be performed in any order, and/or with two or more of introduction/modification performed concurrently. These cells are able to grow in medium containing xylose as the sole carbon source. More typically, these cells are grown in medium containing xylose as well as other sugars such as glucose and arabinose. This allows effective use of the sugars found in a hydrolysate medium that is prepared from cellulosic biomass by pretreatment and saccharification.

In further embodiments the described nucleic acid molecule is introduced into a yeast cell which has a metabolic pathway that produces a target chemical. Introduction of xylose isomerase activity and the metabolic pathway may be performed in any order, and/or with two or more genetic modifications performed concurrently. Examples of target compounds include ethanol, butanol, and 1,3-propanediol. Yeast cells containing metabolic pathways for production of target chemicals are described above.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

The meaning of abbreviations is as follows: "kb" means kilobase(s), "bp" means base pairs, "nt" means nucleotide(s), "hr" means hour(s), "min" means minute(s), "sec" means second(s), "d" means day(s), "L" means liter(s), "ml" or "mL" means milliliter(s), "µL" means microliter(s), "µg" means microgram(s), "ng" means nanogram(s), "mg" means milligram(s), "mM" means millimolar, "µM" means micromolar, "nm" means nanometer(s), "µmol" means micromole(s), "pmol" means picomole(s), "XI" is xylose isomerase, "nt" means nucleotide.

Standard recombinant DNA and molecular cloning techniques used here are well known in the art and are described by Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987), and by *Methods in Yeast Genetics*, 2005, Cold Spring Harbor Laboratory Press, Cold Spring Harbor, N.Y.

HPLC Analysis

Cell culture samples were taken at timed intervals and analyzed for EtOH and xylose using either a Waters HPLC system (Alliance system, Waters Corp., Milford, Mass.) or an Agilent 1100 Series LC; conditions=0.6 mL/min of 0.01 N $H_2SO_4$, injection volume=10 µL, autosampler temperature=10° C., column temperature=65° C., run time=25 min, detection by refractive index (maintained at 40° C.). The HPLC column was purchased from BioRad (Aminex HPX-87H, BioRad Inc., Hercules, Calif.). Analytes were quantified by refractive index detection and compared to known standards.

Example 1

Up-Regulation of the Native Pentose Pathway in S. cerevisiae

In addition to expression of an active xylose isomerase enzyme, a robust pentose pathway is necessary for efficient use of xylose and ethanol production under oxygen-limiting conditions in S. cerevisiae. The pentose pathway consists of five enzymes. In S. cerevisiae, these proteins are xylulokinase (XKS1), transaldolase (TAL1), transketolase 1 (TKL1), D-ribulose-5-phosphate 3-epimerase (RPE1), and ribose 5-phosphate ketol-isomerase (RKI1). In order to increase the expression of these proteins, their coding regions from the S. cerevisiae genome were cloned for expression under different promoters and integrated in the S. cerevisiae chromosome. The GRE3 locus encoding aldose reductase was chosen for integration. To construct such this strain, the first step was the construction of an integration vector called P5 Integration Vector in GRE3.

The sequence of the P5 Integration Vector in GRE3 is given as SEQ ID NO:14, and the following numbers refer to nucleotide positions in this vector sequence. Gaps between the given nt numbers include sequence regions containing restriction sites. The TAL1 coding region (15210 to 16217) was expressed with the TPI1 promoter (14615 to 15197) and uses the TAL1t terminator. The RPE1 (13893 to 14609) coding region was expressed with the FBA1 promoter (13290 to 13879) and uses the terminator at the upstream end of the TPI1 promoter. RKI1 coding region (nt 11907 to 12680) was expressed with the TDH3 promoter (11229 to 11900) and uses the GPDt (previously called TDH3t) terminator. The TKL1 coding region (nt 8830 to 10872) was expressed with the PGK1 promoter (nt 8018 to 8817) and uses the TKL1t terminator. The XKS1 coding region (nt 7297 to 5495 to) was expressed with the Ilv5 promoter (nt 8009 to 7310) and uses the ADH terminator. In this integration vector, the URA3 marker (nt 332 to 1135) was flanked by loxP sites (nt 42 to 75 and nt 1513 to 1546) for recycling of the marker. The vector contains integration arms for the GRE3 locus (nt 1549 to 2089 and nt 4566 to 5137). This P5 Integration Vector in GRE3 can be linearized by digesting with the KasI enzyme before integration.

The yeast strain chosen for this study was BP1548 which is a haploid strain derived from prototrophic diploid strain CBS 8272 (Centraalbureau voor Schimmelcultures (CBS) Fungal Biodiversity Centre, Netherlands). This strain is in the CEN.PK lineage of Saccharomyces cerevisiae strains. BP1548 contains the MATα mating type and deletions of the URA3 and HIS3 genes.

To produce BP1548, first CBS 8272 was sporulated and a tetrad was dissected to yield four haploid strains using standard procedures (Amberg et al., Methods in Yeast Genetics, 2005). One of the MATα haploids, PNY0899, was selected for further modifications. The URA3 coding sequence (ATG through stop codon) and 130 bp of sequence upstream of the URA3 coding sequence was deleted by homologous recombination using a KanMX deletion cassette flanked by loxP sites, primer binding sites, and homologous sequences outside of the URA3 region to be deleted. After removal of the KanMX marker using the cre recombinase, a 95 bp sequence consisting of a loxP site flanked by the primer binding sites remained as a URA3 deletion scar in the genome (SEQ ID NO:15). This sequence is located in the genome between URA3 upstream sequence (SEQ ID NO:16) and URA3 downstream sequence (SEQ ID NO:17). The HIS3 coding sequence (ATG up to the stop codon) was deleted by homologous recombination using a scarless method. The deletion joins genomic sequences that were originally upstream (SEQ ID NO:18) and downstream (SEQ ID NO:19) of the HIS3 coding sequence. The KasI integration fragment containing all five pentose pathway genes in vector P5 Integration Vector in GRE3 was transformed into the BP1548 strain using the Frozen-EZ Yeast Transformation II Kit from Zymo Research (Irvine, Calif.). Transformants were selected on synthetic dropout (SD) medium lacking uracil. To recycle the URA3 marker, the CRE recombinase vector pJT254 (SEQ ID NO:20) was transformed into these integrated strains. This vector was derived from pRS413 and the cre coding region (nt 2562 to 3593) was under the control of the GAL1 promoter (nt 2119 to 2561). Strains that could no longer grow on SD (-uracil) medium were selected. Further passages on YPD medium was used to cure the plasmid pJT257. The resulting strain was designated as C52-79.

Example 2

Selection and Expression of Bacterial Xylose Isomerases

In order to identify candidate bacterial xylose isomerases that may be active when expressed in yeast, we used amino acid sequences of the xylose isomerases from Ruminococcus flavefaciens FD-1 (SEQ ID NO:11) and from Ruminococcus champanellensis 18P13 (SEQ ID NO:9) in a BLAST search against translated open reading frames of the metagenomic database generated from cow rumen (Matthias Hess, et al. Science 331:463-467 (2011)). These two proteins have 77% amino acid identity to each other. No proteins sequences were found to have greater than 70% identity to either of these sequences. Based on this search, four putative xylose isomerases from among the sequences with closest identities were chosen for further study and named Ru1 (SEQ ID NO:3) Ru2 (SEQ ID NO:5), Ru3 (SEQ ID NO:7), and Ru4 (SEQ ID NO:1). DNA sequences encoding these proteins were designed using codon optimization for expression in S. cerevisiae, given designations of xylA (Ru1) (SEQ ID NO:4), xylA(Ru2) (SEQ ID NO:6), xylA(Ru3) (SEQ ID NO:8), and xylA(Ru4) (SEQ ID NO:2), respectively, and the designed nucleic acid molecules were synthesized. A 5' PmeI site and 3' SfiI site was added during the synthesis of the coding regions. In addition, a codon-optimized coding region for the Ruminococcus champanellensis 18P13 xylose isomerase was synthesized and named xyl(A-10) (SEQ ID NO:10).

The synthesized xylA coding regions xylA(Ru2), xylA (Ru3), xylA(Ru4), and xylA-10 were expressed using a 1,184-nt promoter of the S. cerevisiae acetohydroxyacid reductoisomerase gene (ILV5p) and a 635-nt terminator of the S. cerevisiae acetohydroxyacid reductoisomerase gene (ILV5t). The chimeric genes were located between NotI and XhoI sites in a pHR81-based shuttle vector, with the coding region between PmeI and SfiI sites. The pHR81 vector (ATCC #87541) contains a pMB1 origin and an ampicillin resistance (ampR) marker to allow plasmid propagation and selection, respectively, in E. coli. In addition, pHR81 has a 2 micron replication origin, a URA3 selection marker, and LEU 2-d for propagation and selection in yeast, which gives high copy number in S. cerevisiae when grown in medium lacking leucine. The sequence of the pHR81 vector containing the ILVp-xylA(Ru2)-ILV5t chimeric gene is SEQ ID NO:13.

Vectors containing the other coding regions are identical with the exception of the substitution of each separate coding region between ILV5p and ILV5t, between PmeI and SfiI sites. The xylA(Ru2) vector was named pHR81 ilv5p xylA (Ru2), with other vectors having the same name, except substituting the specific xylA coding region designation. These constructs were transformed into the C52-79 strain (Example 1) and transformants were selected on plates containing synthetic glucose medium lacking uracil: 6.7 g/L yeast nitrogen base without amino acids (Amresco, Solon, Ohio), 0.77 g/L minus ura Drop Out supplement (Clontech Laboratories, Mountain View, Calif.), 20 g/L glucose. Transformants were then tested for growth and ethanol production.

Example 3

Growth and Ethanol Production in *S. cerevisiae* Containing Different Bacterial Xylose Isomerases

*S. cerevisiae* strain C52-79 (Example 1) lacks the ability to use xylose as the energy and carbon source since it lacks xylose isomerase activity. Yeast strains expressing xylA (Ru2), xylA(Ru3), xylA(Ru4), and xylA-10 chimeric genes were tested in YPX medium (10 g/l yeast extract, 20 g/l peptone, and 40 g/l of xylose). To perform this test, strains were inoculated into 10 ml of YPX medium in 50 ml tissue culture tubes at a starting $OD_{600}$ of 0.5. The lids were tightly closed and the tubes were placed in a 30° C. rotary shaker set at a speed of 225 rpm. At different time intervals (24 hr, 44 hr, and 72 hr), samples were taken and the xylose and ethanol concentrations were determined by HPLC analysis as described in General Methods, as well as recording the $OD_{600}$. Three individual cultures for each strain were grown and analyzed. The results were averaged for each set of 3 replicates, and are given in Table 3.

TABLE 3

Growth, xylose consumption, and ethanol production of yeast strain expressing various xylose isomerases

| Vector in Strain | $OD_{600}$ | | Xylose consumed (g/L) | | Ethanol Produced (g/L) | |
|---|---|---|---|---|---|---|
| | Av. | SD | Av. | SD | Av. | SD |
| After 24 hours | | | | | | |
| pHR81 ilv5p xylA(Ru4) | 6.54 | 0.30 | 7.65 | 0.72 | 2.57 | 0.30 |
| pHR81 ilv5p xylA(Ru2) | 2.41 | 0.86 | 0.60 | 0.19 | 0.00 | 0.00 |
| pHR81 ilv5p xylA(Ru3) | 2.69 | 0.12 | 0.60 | 0.08 | 0.00 | 0.00 |
| pHR81 ilv5p xylA(xylA10) | 3.00 | 0.41 | 0.40 | 0.13 | 0.00 | 0.00 |
| After 44 hours | | | | | | |
| pHR81 ilv5p xylA(Ru4) | 12.55 | 0.09 | 39.41 | 0.96 | 15.49 | 0.43 |
| pHR81 ilv5p xylA(Ru2) | 3.03 | 0.41 | 0.63 | 0.18 | 0.00 | 0.00 |
| pHR81 ilv5p xylA(Ru3) | 3.24 | 0.20 | 0.58 | 0.02 | 0.00 | 0.00 |
| pHR81 ilv5p xylA(xylA10) | 3.22 | 0.50 | 0.64 | 0.12 | 0.00 | 0.00 |

TABLE 3-continued

Growth, xylose consumption, and ethanol production of yeast strain expressing various xylose isomerases

| Vector in Strain | $OD_{600}$ | | Xylose consumed (g/L) | | Ethanol Produced (g/L) | |
|---|---|---|---|---|---|---|
| | Av. | SD | Av. | SD | Av. | SD |
| After 72 hours | | | | | | |
| pHR81 ilv5p xylA(Ru2) | 3.10 | 0.22 | 0.78 | 0.16 | 0.00 | 0.00 |
| pHR81 ilv5p xylA(Ru3) | 2.82 | 0.18 | 1.13 | 0.25 | 0.00 | 0.00 |
| pHR81 ilv5p xylA(xylA10) | 3.02 | 0.13 | 1.00 | 0.10 | 0.00 | 0.00 |

As shown in Table 3, yeast strains containing the chimeric gene for expression of Ru4 consumed xylose and at the same time, produced ethanol when measured at 24 hours. After 44 hours of incubation essentially all of the xylose was consumed and over 15 g/L of ethanol was produced by this strain. These results indicate that Ru4 was expressed as an active the xylose isomerase enzyme in *S. cerevisiae*. Strains expressing other xylAs, however, consumed almost no xylose and did not produce ethanol even after 72 hours. The highest sequence identity compared to Ru4 of a tested amino acid sequence that did not provide xylose isomerase activity is 80%, which is to Ru3.

Example 4

Expression of Additional Xylose Isomerase

The synthesized xylA(Ru1) coding region (Example 2) was cloned, transformed into strain C52-79, and the resulting strain assayed as described in Examples 2 and 3. The results are given in Table 4.

TABLE 4

Growth, xylose consumption, and ethanol production of yeast strains expressing Ru1

| Vector in Strain | $OD_{600}$ | | Xylose consumed (g/L) | | Ethanol Produced (g/L) | |
|---|---|---|---|---|---|---|
| | Av. | SD | Av. | SD | Av. | SD |
| After 24 hours | | | | | | |
| pHR81 ilv5p xylA(Ru1) | 9.6 | 0.36 | 21.56 | 3.88 | 8.25 | 1.79 |
| After 44 hours | | | | | | |
| pHR81 ilv5p xylA(Ru1) | 12.72 | 0.43 | 39.92 | 0.00 | 16.09 | 0.10 |

As shown in Table 4, the yeast strain containing the chimeric gene for expression of Ru1 consumed xylose and at the same time, produced ethanol when measured at 24 hours. After 44 hours of incubation essentially all of the xylose was consumed and over 16 g/L of ethanol was produced by this strain. These results indicate that Ru1 was expressed as an active the xylose isomerase enzyme in *S. cerevisiae*.

What is claimed is:

1. A method for producing a yeast cell that has xylose isomerase activity comprising: a) providing a yeast cell; b) introducing a heterologous nucleic acid molecule encoding a polypeptide having xylose isomerase activity and amino acid sequence with at least 95% sequence identity to the amino acid sequence of SEQ ID NO: 1; wherein a yeast cell having xylose isomerase activity is produced.

2. The method of claim 1 wherein the heterologous nucleic acid molecule is a part of a chimeric gene.

3. The method of claim 1 or 2 wherein the amino acid sequence has at least 95% identity to either of SEQ ID NO: 1 or SEQ ID NO: 3.

4. The method of claim 1 wherein the yeast cell having xylose isomerase activity has a complete xylose utilization pathway and grows in a medium comprising xylose as a carbon source; wherein xylose is utilized.

5. The method of claim 4 wherein the yeast cell comprises a metabolic pathway that produces a target compound.

6. The method of claim 5 wherein the target compound is selected from the group consisting of ethanol, butanol, and 1,3-propanediol.

* * * * *

SEQUENCE LISTING

<160> NUMBER OF SEQ ID NOS: 20

<210> SEQ ID NO 1
<211> LENGTH: 438
<212> TYPE: PRT
<213> ORGANISM: Unknown

<220> FEATURE:
<223> OTHER INFORMATION: uncultured bacteria from cow rumen

<400> SEQUENCE: 1

```
Met Ser Glu Ile Phe Ala Asn Ile Pro Val Ile Pro Tyr Glu Gly Pro
1               5                   10                  15

Gln Ser Lys Asn Pro Leu Ala Phe Lys Phe Tyr Asp Ala Asp Lys Val
            20                  25                  30

Ile Leu Gly Lys Lys Met Ser Glu His Leu Pro Phe Ala Met Ala Trp
        35                  40                  45

Trp His Asn Leu Cys Ala Gly Gly Thr Asp Met Phe Gly Arg Asp Thr
    50                  55                  60

Ala Asp Lys Ser Phe Gly Ala Glu Lys Gly Thr Met Ala His Ala Arg
65                  70                  75                  80

Ala Lys Val Asp Ala Gly Phe Glu Phe Met Lys Lys Val Gly Val Lys
                85                  90                  95

Tyr Phe Cys Phe His Asp Val Asp Leu Val Pro Glu Ala Asp Asp Ile
            100                 105                 110

Lys Glu Thr Asn Arg Arg Leu Asp Glu Ile Ser Asp Tyr Ile Leu Glu
        115                 120                 125

Lys Met Lys Gly Thr Asp Ile Lys Cys Leu Trp Gly Thr Ala Asn Met
    130                 135                 140

Phe Gly Asn Pro Arg Tyr Met Asn Gly Ala Gly Ser Thr Asn Ser Ala
145                 150                 155                 160

Asp Val Phe Cys Phe Ala Ala Ala Gln Ile Lys Lys Ala Leu Asp Leu
                165                 170                 175

Thr Val Lys Leu Gly Gly Arg Gly Tyr Val Phe Trp Gly Gly Arg Glu
            180                 185                 190

Gly Tyr Glu Thr Leu Leu Asn Thr Asp Met Lys Phe Glu Gln Glu Asn
        195                 200                 205

Ile Ala Arg Leu Met His Leu Ala Val Asp Tyr Gly Arg Ser Ile Gly
    210                 215                 220

Phe Thr Gly Asp Phe Tyr Ile Glu Pro Lys Pro Lys Glu Pro Met Lys
225                 230                 235                 240

His Gln Tyr Asp Phe Asp Ala Ala Thr Ala Ile Gly Phe Leu Arg Gln
                245                 250                 255

Tyr Gly Leu Asp Lys Asp Phe Lys Met Asn Ile Glu Ala Asn His Ala
            260                 265                 270

Thr Leu Ala Gly His Thr Phe Gln His Asp Leu Arg Ile Ser Ala Ile
        275                 280                 285

Asn Gly Met Leu Gly Ser Ile Asp Ala Asn Gln Gly Asp Leu Leu Leu
    290                 295                 300

Gly Trp Asp Thr Asp Glu Phe Pro Phe Asn Val Tyr Glu Ala Thr Leu
305                 310                 315                 320

Cys Met Tyr Glu Val Leu Lys Ala Gly Gly Leu Thr Gly Gly Phe Asn
                325                 330                 335

Phe Asp Ser Lys Thr Arg Arg Pro Ser Tyr Thr Leu Glu Asp Met Phe
            340                 345                 350

His Ala Tyr Ile Leu Gly Met Asp Thr Phe Ala Leu Gly Leu Ile Lys
        355                 360                 365

Ala Ala Ala Leu Ile Glu Asp Gly Arg Leu Asp Gln Phe Val Ala Asp
    370                 375                 380

Arg Tyr Ala Ser Tyr Lys Thr Gly Ile Gly Ala Lys Ile Arg Ser Gly
385                 390                 395                 400
```

-continued

Glu Thr Thr Leu Ala Glu Leu Ala Ala Tyr Ala Asp Lys Leu Gly Ala
            405                 410                 415

Pro Ala Leu Pro Ser Ser Gly Arg Gln Glu Tyr Leu Glu Ser Ile Val
        420                 425                 430

Asn Ser Ile Leu Phe Gly
        435

<210> SEQ ID NO 2
<211> LENGTH: 1314
<212> TYPE: DNA
<213> ORGANISM: artificial sequence
<220> FEATURE:
<223> OTHER INFORMATION: coding region for Ru4 optimized for expression
      in Saccharomyces cerevisiae

<400> SEQUENCE: 2

```
atgtctgaaa tcttcgctaa catcccagtc atcccatacg aaggtccaca atctaagaac      60
ccattggctt tcaagttcta cgacgctgac aaggttatct gggtaaaaaa gatgtctgaa     120
cacttgccat tcgctatggc ttggtggcac aacttgtgtg ctggtggtac tgacatgttc     180
ggtagagaca ctgctgataa gtccttcggt gctgaaaagg gtactatggc tcacgctaga     240
gctaaggttg acgctggttt cgagttcatg aagaaggttg gtgtcaagta cttctgtttc     300
cacgacgttg atttggtccc agaagctgac gatatcaagg aaactaacag aagattggac     360
gaaatctctg attacatctt ggaaagatg aagggtactg acatcaagtg tttgtggggt     420
actgctaaca tgttcggtaa cccaagatac atgaacggtg ctggttctac caactccgct     480
gacgttttct gtttcgctgc tgctcaaatc aagaaggctt ggatttgac tgttaagttg     540
ggtggtagag gttacgtctt ctggggtggt agagaaggtt acgaaacctt gttgaacact     600
gacatgaagt cgaacaaga aaacatcgct agattgatgc acttggctgt tgactacggt     660
agatctatcg gtttcaccgg tgacttctac atcgaaccaa agccaaagga accaatgaag     720
caccaatacg acttcgatgc tgctactgct atcggtttct tgagacaata cggtttggac     780
aaggatttca gatgaacat cgaagctaac cacgctacct ggctggtca cactttccaa     840
cacgacttga aatctctgc tatcaacggt atgttgggtt ccatcgacgc taaccaaggt     900
gacttgttgt tgggttggga caccgatgaa tttccattca acgtttacga agctactttg     960
tgtatgtacg aagtcttgaa ggctggtggt ttgaccggtg gtttcaactt cgactctaag    1020
accagaagac catcctacac tttggaagac atgttccacg cttacatctt gggtatggat    1080
actttcgctt gggtttgat caaggctgct gctttgatcg aagacggtag attggatcaa    1140
ttcgttgctg acagatacgc ttcttacaag accggtatcg gtgctaagat cagatccggt    1200
gaaaccactt tggctgaatt ggctgcttac gctgacaagt tgggtgctcc agctttgcca    1260
tcttccggta gacaagaata cttggaatct atcgtcaact ccatcttgtt cggt          1314
```

<210> SEQ ID NO 3
<211> LENGTH: 438
<212> TYPE: PRT
<213> ORGANISM: Unknown
<220> FEATURE:
<223> OTHER INFORMATION: uncultured bacteria from cow rumen

<400> SEQUENCE: 3

Met Ala Glu Ile Phe Lys Gly Ile Pro Glu Ile Arg Tyr Glu Gly Pro
1               5                   10                  15

Asn Ser Thr Asn Pro Leu Ser Phe Lys Tyr Tyr Asp Pro Asp Lys Val
            20                  25                  30

```
Ile Leu Gly Lys Pro Met Lys Glu His Leu Pro Phe Ala Met Ala Trp
         35                  40                  45

Trp His Asn Leu Gly Ala Ala Gly Thr Asp Met Phe Gly Arg Asp Thr
     50                  55                  60

Ala Asp Lys Ser Phe Gly Ala Glu Lys Gly Thr Met Glu His Ala Lys
 65                  70                  75                  80

Ala Lys Val Asp Ala Gly Phe Glu Phe Met Lys Lys Leu Gly Ile Arg
                 85                  90                  95

Tyr Phe Cys Phe His Asp Val Asp Leu Val Pro Glu Ala Asp Asp Ile
             100                 105                 110

Lys Val Thr Asn Ala Arg Leu Asp Glu Ile Ser Asp Tyr Ile Leu Glu
         115                 120                 125

Lys Met Lys Gly Thr Asp Ile Lys Cys Leu Trp Gly Thr Ala Asn Met
     130                 135                 140

Phe Ser Asn Pro Arg Phe Met Asn Gly Ala Gly Ser Thr Asn Ser Ala
145                 150                 155                 160

Asp Val Phe Cys Phe Ala Ala Ala Gln Val Lys Lys Ala Leu Asp Ile
                 165                 170                 175

Thr Val Lys Leu Gly Gly Lys Gly Tyr Val Phe Trp Gly Gly Arg Glu
             180                 185                 190

Gly Tyr Glu Thr Leu Leu Asn Thr Asp Val Lys Phe Glu Gln Glu Asn
         195                 200                 205

Ile Ala Lys Leu Met His Leu Ala Val Asp Tyr Gly Arg Ser Ile Gly
     210                 215                 220

Phe Lys Gly Asp Phe Phe Ile Glu Pro Lys Pro Lys Glu Pro Met Lys
225                 230                 235                 240

His Gln Tyr Asp Phe Asp Ala Ala Thr Ala Ile Gly Phe Val Arg Gln
                 245                 250                 255

Tyr Gly Leu Asp Lys Asp Phe Lys Met Asn Ile Glu Ala Asn His Ala
             260                 265                 270

Thr Leu Ala Gly His Thr Phe Gln His Glu Leu Arg Ile Ser Ala Ile
         275                 280                 285

Asn Gly Met Leu Gly Ser Ile Asp Ala Asn Gln Gly Asp Met Leu Leu
     290                 295                 300

Gly Trp Asp Thr Asp Glu Phe Pro Phe Asn Val Tyr Asp Thr Thr Leu
305                 310                 315                 320

Cys Met Tyr Glu Val Leu Lys Asn Gly Gly Ile Pro Gly Gly Phe Asn
                 325                 330                 335

Phe Asp Ala Lys Asn Arg Arg Pro Ser Tyr Thr Ala Glu Asp Met Phe
             340                 345                 350

Tyr Gly Phe Ile Leu Gly Met Asp Ser Phe Ala Leu Gly Leu Ile Lys
         355                 360                 365

Ala Ala Lys Leu Ile Glu Asp Gly Arg Ile Asp Lys Phe Val Glu Glu
     370                 375                 380

Arg Tyr Ala Ser Tyr Lys Asp Gly Ile Gly Lys Lys Ile Arg Asp Gly
385                 390                 395                 400

Glu Thr Thr Leu Ala Glu Leu Ala Ala Tyr Ala Asp Gln Leu Gly Ala
                 405                 410                 415

Pro Lys Leu Pro Gly Ser Gly Arg Gln Glu Asp Leu Glu Ser Val Phe
             420                 425                 430

Asn Gln Val Leu Phe Gly
         435
```

<210> SEQ ID NO 4
<211> LENGTH: 1314
<212> TYPE: DNA
<213> ORGANISM: artificial sequence
<220> FEATURE:
<223> OTHER INFORMATION: coding region for Ru1 optimized for expression in Saccharomyces cerevisiae

<400> SEQUENCE: 4

| | | |
|---|---|---|
| atggctgaaa tcttcaaggg tatcccagaa atcagatacg aaggtccaaa ctccactaac | 60 |
| ccattgtctt tcaagtacta cgatccagac aaggttatct gggtaaaacc aatgaaggaa | 120 |
| cacttgccat cgctatggc ttggtggcac aacttgggtg ctgctggtac tgacatgttc | 180 |
| ggtagagaca ctgctgataa gtctttcggt gctgaaaagg gtactatgga acacgctaag | 240 |
| gctaaggttg acgctggttt cgagttcatg aagaagttgg gtatcagata cttctgtttc | 300 |
| cacgacgttg atttggtccc agaagctgac gatatcaagg tcactaacgc tagattggac | 360 |
| gaaatctctg attacatctt ggaaaagatg aagggtactg acatcaagtg tttgtggggt | 420 |
| actgctaaca tgttctccaa cccaagattc atgaacggtg ctggttctac caactccgct | 480 |
| gacgttttct gttcgctgc tgctcaagtc aagaaggctt tggacatcac tgttaagttg | 540 |
| ggtggtaaag gttacgtctt ctggggtggt agagaaggtt acgaaacctt gttgaacact | 600 |
| gacgttaagt tcgaacaaga aaacatcgct aagttgatgc acttggctgt tgactacggt | 660 |
| agatctatcg gtttcaaggg tgacttcttc atcgaaccaa agccaaagga accaatgaag | 720 |
| caccaatacg acttcgatgc tgctaccgct atcggtttcg ttagacaata cggtttggac | 780 |
| aaggatttca gatgaacat cgaagctaac cacgctacct ggctggtca cactttccaa | 840 |
| cacgaattga gaatctctgc tatcaacggt atgttgggtt ccatcgacgc taaccaaggt | 900 |
| gacatgttgt tgggttggga caccgatgaa tttccattca acgtttacga caccactttg | 960 |
| tgtatgtacg aagtcttgaa gaacggtggt atcccaggtg gtttcaactt cgacgctaag | 1020 |
| aacagaagac catcttacac tgctgaagac atgttctacg gtttcatctt gggtatggat | 1080 |
| tccttcgctt ggggttttgat caaggctgct aagttgatcg aagacggtag aatcgataag | 1140 |
| ttcgtcgaag aaagatacgc ttcttacaag gacggtatcg gtaaaaagat cagagatggt | 1200 |
| gaaaccactt tggctgaatt ggctgcttac gctgaccaat gggtgctcc aaagttgcca | 1260 |
| ggttctggta gacaagaaga cttggaatcc gttttcaacc aagtcttgtt cggt | 1314 |

<210> SEQ ID NO 5
<211> LENGTH: 439
<212> TYPE: PRT
<213> ORGANISM: Unknown
<220> FEATURE:
<223> OTHER INFORMATION: uncultured bacteria from cow rumen

<400> SEQUENCE: 5

Met Gly Glu Ile Phe Ser Asn Ile Pro Val Ile Lys Tyr Glu Gly Pro
1               5                   10                  15

Asp Ser Lys Asn Pro Leu Ala Phe Lys Tyr Tyr Asp Pro Glu Arg Val
            20                  25                  30

Ile Leu Gly Lys Lys Met Lys Glu His Leu Pro Phe Ala Met Ala Trp
        35                  40                  45

Trp His Asn Leu Cys Ala Asn Gly Val Asp Met Phe Gly Arg Gly Thr
    50                  55                  60

Ile Asp Lys Leu Phe Gly Ala Ala Glu Ala Gly Thr Met Glu His Ala
65                  70                  75                  80

```
Lys Ala Lys Val Asp Ala Gly Ile Glu Phe Met Gln Lys Leu Gly Ile
                85                  90                  95

Glu Tyr Tyr Cys Phe His Asp Val Asp Leu Val Pro Glu Ala Asp Asp
            100                 105                 110

Ile Asn Glu Thr Asn Arg Arg Leu Asp Glu Leu Thr Asp Tyr Leu Lys
        115                 120                 125

Glu Lys Thr Ala Gly Thr Asn Ile Lys Cys Leu Trp Gly Thr Ala Asn
130                 135                 140

Met Phe Ser Asn Pro Arg Phe Met Asn Gly Ala Gly Ser Thr Asn Asp
145                 150                 155                 160

Val Asp Val Tyr Cys Phe Ala Ala Gln Val Lys Lys Ala Ile Glu
                165                 170                 175

Met Thr Val Lys Leu Gly Gly Arg Gly Tyr Val Phe Trp Gly Gly Arg
            180                 185                 190

Glu Gly Tyr Glu Thr Leu Leu Asn Thr Lys Val Gln Met Glu Leu Glu
        195                 200                 205

Asn Ile Ala Asn Leu Met Lys Met Ala Arg Asp Tyr Gly Arg Ser Ile
    210                 215                 220

Gly Phe Lys Gly Thr Phe Leu Ile Glu Pro Lys Pro Lys Glu Pro Met
225                 230                 235                 240

Lys His Gln Tyr Asp Tyr Asp Ala Ala Thr Ala Ile Gly Phe Leu Arg
                245                 250                 255

Gln Tyr Gly Leu Asp Gln Asp Phe Lys Met Asn Ile Glu Ala Asn His
            260                 265                 270

Ala Thr Leu Ala Gly His Thr Phe Gln His Glu Leu Arg Ile Ser Arg
        275                 280                 285

Ile Asn Gly Met Leu Gly Ser Ile Asp Ala Asn Gln Gly Asp Ile Met
    290                 295                 300

Leu Gly Trp Asp Thr Asp Cys Phe Pro Ser Asn Val Tyr Asp Thr Thr
305                 310                 315                 320

Leu Ala Met Tyr Glu Ile Val Arg Asn Gly Gly Leu Pro Val Gly Ile
                325                 330                 335

Asn Phe Asp Ser Lys Asn Arg Arg Pro Ser Asn Thr Tyr Glu Asp Met
            340                 345                 350

Phe His Ala Phe Ile Leu Gly Met Asp Ser Phe Ala Phe Gly Leu Ile
        355                 360                 365

Lys Ala Ala Gln Ile Ile Glu Asp Gly Arg Ile Glu Gly Phe Thr Glu
    370                 375                 380

Lys Lys Tyr Glu Ser Phe Asn Thr Glu Leu Gly Gln Lys Ile Arg Lys
385                 390                 395                 400

Gly Glu Ala Thr Leu Glu Glu Leu Ala Ala His Ala Ala Asp Leu Lys
                405                 410                 415

Ala Pro Lys Val Pro Val Ser Gly Arg Gln Glu Tyr Leu Glu Gly Val
            420                 425                 430

Leu Asn Asn Ile Ile Leu Ser
        435
```

<210> SEQ ID NO 6
<211> LENGTH: 1317
<212> TYPE: DNA
<213> ORGANISM: artificial sequence
<220> FEATURE:
<223> OTHER INFORMATION: coding region for Ru2 optimized for expression in Saccharomyces cerevisiae

<400> SEQUENCE: 6

```
atgggtgaaa tcttctctaa catcccagtc atcaagtacg aaggtccaga ctctaagaac    60
ccattggctt tcaagtacta cgatccagaa agagtcatct tgggtaaaaa gatgaaggaa   120
cacttgccat tcgctatggc ttggtggcac aacttgtgtg ctaacggtgt tgacatgttc   180
ggtagaggta ctatcgataa gttgttcggt gctgctgaag ctggtactat ggaacacgct   240
aaggctaagg ttgacgctgg tatcgagttc atgcaaaagt tgggtatcga atactactgt   300
ttccacgacg ttgatttggt cccagaagct gacgatatca acgaaaccaa cagaagattg   360
gacgaattga ctgattactt gaaggaaaag accgctggta ctaacatcaa gtgtttgtgg   420
ggtactgcta acatgttctc taacccaaga ttcatgaacg gtgctggttc cactaacgac   480
gttgatgtct actgtttcgc tgctgctcaa gttaagaagg ctatcgaaat gaccgtcaag   540
ttgggtggta gaggttacgt tttctggggt ggtagagaag gttacgaaac cttgttgaac   600
actaaggtcc aaatggaatt ggaaaacatc gctaacttga tgaagatggc tagagactac   660
ggtagatcta tcggtttcaa gggtactttc ttgatcgaac aaagccaaa ggaaccaatg    720
aagcaccaat acgactacga tgctgctact gctatcggtt tcttgagaca atacggtttg   780
gaccaagatt tcaagatgaa catcgaagct aaccacgcta ccttggctgg tcacactttc   840
caacacgaat tgagaatctc tagaatcaac ggtatgttgg gttccatcga cgctaaccaa   900
ggtgacatca tgttgggttg ggacaccgat tgtttcccat ctaacgttta cgacaccact   960
ttggctatgt acgaaatcgt tagaaacggt ggtttgccag tcggtatcaa cttcgactct  1020
aagaacagaa gaccatccaa cacttacgaa gacatgttcc acgctttcat cttgggtatg  1080
gactctttcg ctttcggttt gatcaaggct gctcaaatca tcgaagacgg tagaatcgaa  1140
ggtttcaccg aaaagaagta cgaatccttc aacactgaat gggtcaaaa gatcagaaag   1200
ggtgaagcta ctttggaaga attggctgct cacgctgctg acttgaaggc tccaaaggtt  1260
ccagtctctg gtagacaaga atacttggaa ggtgttttga caacatcat cttgtcc       1317
```

<210> SEQ ID NO 7
<211> LENGTH: 395
<212> TYPE: PRT
<213> ORGANISM: Unknown
<220> FEATURE:
<223> OTHER INFORMATION: uncultured bacteria from cow rumen

<400> SEQUENCE: 7

```
Met Ala Trp Trp His Asn Met Cys Ala Asn Gly Lys Asp Met Phe Gly
1               5                   10                  15

Thr Gly Thr Ala Asp Lys Ser Phe Gly Ala Glu Pro Gly Thr Met Glu
            20                  25                  30

His Ala Lys Ala Lys Val Asp Ala Ile Glu Phe Met Gln Lys Leu
        35                  40                  45

Gly Ile Glu Tyr Tyr Cys Phe His Asp Val Asp Leu Val Pro Glu Asp
    50                  55                  60

Glu Asp Asp Ile Asn Val Thr Asn Ala Arg Leu Asp Glu Ile Ser Asp
65                  70                  75                  80

Tyr Ile Leu Glu Lys Thr Lys Gly Thr Asn Ile Arg Cys Leu Trp Gly
                85                  90                  95

Thr Ala Asn Met Phe Asn Asn Pro Arg Phe Met Asn Gly Ala Gly Ser
            100                 105                 110

Thr Asn Ser Ala Asp Val Tyr Cys Phe Ala Ala Ala Gln Ile Lys Lys
        115                 120                 125
```

```
Ala Leu Asp Ile Thr Val Lys Leu Gly Gly Arg Gly Tyr Val Phe Trp
         130                 135                 140

Gly Gly Arg Glu Gly Tyr Glu Thr Leu Leu Asn Thr Asp Val Lys Leu
145                 150                 155                 160

Glu Gln Glu Asn Ile Ala Asn Leu Met His Met Ala Val Glu Tyr Gly
                 165                 170                 175

Arg Ser Ile Gly Phe Lys Gly Asp Phe Leu Ile Glu Pro Lys Pro Lys
             180                 185                 190

Glu Pro Met Lys His Gln Tyr Asp Phe Asp Ala Ala Thr Ala Ile Gly
         195                 200                 205

Phe Leu Arg Gln Tyr Gly Leu Asp Lys Asp Phe Lys Leu Asn Ile Glu
     210                 215                 220

Ala Asn His Ala Thr Leu Ala Gly His Thr Phe Gln His Glu Leu Arg
225                 230                 235                 240

Ile Ser Ala Met Asn Gly Met Leu Gly Ser Ile Asp Ala Asn Gln Gly
                 245                 250                 255

Asp Met Leu Leu Gly Trp Asp Thr Asp Glu Phe Pro Phe Asn Val Tyr
             260                 265                 270

Asp Thr Thr Leu Ala Met Tyr Glu Val Leu Lys Ala Gly Gly Ile Asn
         275                 280                 285

Gly Gly Phe Asn Phe Asp Ser Lys Asn Arg Arg Pro Ser Asn Thr Tyr
     290                 295                 300

Glu Asp Met Phe Tyr Gly Tyr Ile Leu Gly Met Asp Ser Phe Ala Leu
305                 310                 315                 320

Gly Leu Ile Lys Ala Ala Ile Ile Glu Asp Gly Arg Ile Glu Lys
                 325                 330                 335

Gln Leu Ala Asp Arg Tyr Ser Tyr Ser Asn Thr Glu Ile Gly Lys
             340                 345                 350

Lys Ile Arg Asn His Thr Ala Thr Leu Lys Glu Leu Ala Glu Tyr Ala
         355                 360                 365

Ala Thr Leu Lys Lys Pro Gly Asp Pro Gly Ser Gly Arg Gln Glu Leu
     370                 375                 380

Leu Glu Gln Ile Met Asn Glu Val Met Phe Gly
385                 390                 395

<210> SEQ ID NO 8
<211> LENGTH: 1185
<212> TYPE: DNA
<213> ORGANISM: artificial sequence
<220> FEATURE:
<223> OTHER INFORMATION: coding region for Ru3 optimized for expression
      in Saccharomyces cerevisiae

<400> SEQUENCE: 8
atggcttggt ggcacaacat gtgtgctaac ggcaaggata tgttcggtac tggtactgct      60
gataagtctt tcggtgctga accaggcacc atggaacacg ctaaggctaa ggttgacgct     120
gctatcgagt tcatgcaaaa gttgggtatc gaatactact gtttccacga cgttgatttg     180
gtcccagaag acgaagacga tatcaacgtc actaacgcta gattggacga aatctctgat     240
tacatcttgg aaaagaccaa gggtactaac atcagatgtt gtggggtac tgctaacatg     300 ttcaacaacc caagattcat gaacggtgct ggttctacta actccgctga cgtttactgt     360
ttcgctgctg ctcaaatcaa gaaggctttg gacatcaccg ttaagttggg tggtagaggt     420
tacgtcttct ggggtggtag agaaggttac gaaaccttgt tgaacactga cgttaagttg     480
```

```
gaacaagaaa acatcgctaa cttgatgcac atggctgtcg aatacggtag atctatcggt    540
ttcaagggtg acttcttgat cgaaccaaag ccaaaggaac caatgaagca ccaatacgac    600
ttcgatgctg ctactgctat cggtttcttg agacaatacg gtttggacaa ggatttcaag    660
ttgaacatcg aagctaacca cgctaccttg gctggtcaca ctttccaaca cgaattgaga    720
atctctgcta tgaacggtat gttgggttcc atcgacgcta accaaggtga catgttgttg    780
ggttgggaca ccgatgaatt tccattcaac gtttacgaca ccactttggc tatgtacgaa    840
gtcttgaagg ctggtggtat caacggtggt ttcaacttcg actctaagaa cagaagacca    900
tccaacactt acgaagacat gttctacggt tacatcttgg gtatggattc tttcgctttg    960
ggtttgatca aggctgctgc tatcatcgaa gacggtagaa tcgaaaagca attggctgat   1020
agatactctt cctactccaa caccgaaatc ggtaaaaaga tcagaaacca caccgctact   1080
ttgaaggaat tggctgaata cgctgctact ttgaagaagc caggtgaccc aggttccggt   1140
agacaagaat gttggaaaca atcatgaacg aagttatgt tcggt                    1185
```

<210> SEQ ID NO 9
<211> LENGTH: 441
<212> TYPE: PRT
<213> ORGANISM: Ruminococcus champanellensis

<400> SEQUENCE: 9

```
Met Ser Glu Phe Phe Thr Gly Ile Ser Lys Ile Pro Phe Glu Gly Lys
1               5                   10                  15

Ala Ser Asn Asn Pro Met Ala Phe Lys Tyr Tyr Asn Pro Asp Glu Val
            20                  25                  30

Val Gly Gly Lys Thr Met Arg Glu Gln Leu Lys Phe Ala Leu Ser Trp
        35                  40                  45

Trp His Thr Met Gly Gly Asp Gly Thr Asp Met Phe Gly Val Gly Thr
    50                  55                  60

Thr Asn Lys Lys Phe Gly Gly Thr Asp Pro Met Asp Ile Ala Lys Arg
65                  70                  75                  80

Lys Val Asn Ala Ala Phe Glu Leu Met Asp Lys Leu Ser Ile Asp Tyr
                85                  90                  95

Phe Cys Phe His Asp Arg Asp Leu Ala Pro Glu Ala Asp Asn Leu Lys
            100                 105                 110

Glu Thr Asn Gln Arg Leu Asp Glu Ile Thr Glu Tyr Ile Ala Gln Met
        115                 120                 125

Met Gln Leu Asn Pro Asp Lys Lys Val Leu Trp Gly Thr Ala Asn Cys
    130                 135                 140

Phe Gly Asn Pro Arg Tyr Met His Gly Ala Gly Thr Ala Pro Asn Ala
145                 150                 155                 160

Asp Val Phe Ala Phe Ala Ala Gln Ile Lys Lys Ala Ile Glu Ile
                165                 170                 175

Thr Val Lys Leu Gly Gly Lys Gly Tyr Val Phe Trp Gly Gly Arg Glu
            180                 185                 190

Gly Tyr Glu Thr Leu Leu Asn Thr Asn Met Gly Leu Glu Leu Asp Asn
        195                 200                 205

Met Ala Arg Leu Leu His Met Ala Val Asp Tyr Ala Arg Ser Ile Gly
    210                 215                 220

Phe Thr Gly Asp Phe Tyr Ile Glu Pro Lys Pro Lys Glu Pro Thr Lys
225                 230                 235                 240

His Gln Tyr Asp Phe Asp Thr Ala Thr Val Ile Gly Phe Leu Arg Lys
                245                 250                 255
```

-continued

```
Tyr Asn Leu Asp Lys Asp Phe Lys Met Asn Ile Glu Ala Asn His Ala
            260                 265                 270
Thr Leu Ala Gln His Thr Phe Gln His Glu Leu Arg Val Ala Arg Glu
        275                 280                 285
Asn Gly Phe Phe Gly Ser Ile Asp Ala Asn Gln Gly Asp Thr Leu Leu
    290                 295                 300
Gly Trp Asp Thr Asp Gln Phe Pro Thr Asn Thr Tyr Asp Ala Ala Leu
305                 310                 315                 320
Cys Met Tyr Glu Val Leu Lys Ala Gly Gly Phe Thr Asn Gly Gly Leu
                325                 330                 335
Asn Phe Asp Ser Lys Ala Arg Arg Gly Ser Phe Glu Met Glu Asp Ile
            340                 345                 350
Phe His Ser Tyr Ile Ala Gly Met Asp Thr Phe Ala Leu Gly Leu Lys
        355                 360                 365
Ile Ala Gln Lys Met Ile Asp Asp Gly Arg Ile Asp Gln Phe Val Ala
    370                 375                 380
Asp Arg Tyr Ala Ser Trp Asn Thr Gly Ile Gly Ala Asp Ile Ile Ser
385                 390                 395                 400
Gly Lys Ala Thr Met Ala Asp Leu Glu Ala Tyr Ala Leu Ser Lys Gly
                405                 410                 415
Asp Val Thr Ala Ser Leu Lys Ser Gly Arg Gln Glu Leu Leu Glu Ser
            420                 425                 430
Ile Leu Asn Asn Ile Met Phe Asn Leu
        435                 440
```

<210> SEQ ID NO 10
<211> LENGTH: 1323
<212> TYPE: DNA
<213> ORGANISM: artificial sequence
<220> FEATURE:
<223> OTHER INFORMATION: coding region for R champ XI optimized for expression in Saccharomyces cerevisiae

<400> SEQUENCE: 10

```
atgtccgagt tcttcactgg tatctctaag atcccattcg aaggcaaggc ttctaacaac        60
ccaatggctt tcaagtacta caacccagac gaagttgtcg gtggtaaaac catgagagaa       120
caattgaagt tcgctttgtc ttggtggcac accatgggtg gtgacggtac tgatatgttc       180
ggtgttggta ctactaacaa gaagttcggt ggtactgacc caatggatat cgctaagaga       240
aaggtcaacg ctgctttcga attgatggac aagttgtcca tcgattactt ctgtttccac       300
gacagagatt tggctccaga agctgacaac ttgaaggaaa ccaaccaaag attggatgaa       360
atcactgaat acatcgctca aatgatgcaa ttgaacccag acaagaaggt tttgtggggt       420
actgctaact gtttcggtaa cccaagatac atgcacggtg ctggtactgc tccaaacgct       480
gacgttttcg ctttcgctgc tgctcaaatc aagaaggcta tcgaaatcac cgttaagttg       540
ggtggtaaag gttacgtctt ctggggtggt agagaaggtt acgaaacctt gttgaacact       600
aacatgggtt tggaattgga caacatggct agattgttgc acatggctgt tgactacgct       660
agatctatcg gtttcaccgg tgacttctac atcgaaccaa agccaaagga accaactaag       720
caccaatacg acttcgatac cgctactgtc atcggtttct tgagaaagta caacttggac       780
aaggatttca gatgaacat cgaagctaac cacgctacct ggctcaaca cactttccaa       840
cacgaattga gagttgctag agaaaacggt ttcttcggtt ctatcgacgc taaccaaggt       900
gacaccttgt tgggttggga cactgatcaa ttcccaacca cacttacga cgctgctttg       960
```

```
tgtatgtacg aagtcttgaa ggctggtggt ttcaccaacg gtggtttgaa cttcgactct   1020
aaggctagaa gaggttcctt cgaaatggaa gacatcttcc actcctacat cgctggtatg   1080
gacactttcg ctttgggttt gaagatcgct caaaagatga tcgacgatgg tagaatcgac   1140
caattcgttg ctgatagata cgcttcttgg aacaccggta tcggtgctga catcatctcc   1200
ggtaaagcta ccatggctga cttggaagct tacgctttgt ctaagggtga cgttactgct   1260
tccttgaagt ccggtagaca agaattgttg gaatctatct tgaacaacat catgttcaac   1320
ttg                                                                 1323
```

<210> SEQ ID NO 11
<211> LENGTH: 439
<212> TYPE: PRT
<213> ORGANISM: Ruminococcus flavefaciens

<400> SEQUENCE: 11

```
Met Glu Phe Phe Lys Asn Ile Ser Lys Ile Pro Tyr Glu Gly Lys Asp
1               5                   10                  15

Ser Thr Asn Pro Leu Ala Phe Lys Tyr Tyr Asn Pro Asp Glu Val Ile
            20                  25                  30

Asp Gly Lys Lys Met Arg Asp Ile Met Lys Phe Ala Leu Ser Trp Trp
        35                  40                  45

His Thr Met Gly Gly Asp Gly Thr Asp Met Phe Gly Cys Gly Thr Ala
    50                  55                  60

Asp Lys Thr Trp Gly Glu Asn Asp Pro Ala Ala Arg Ala Lys Ala Lys
65                  70                  75                  80

Val Asp Ala Ala Phe Glu Ile Met Gln Lys Leu Ser Ile Asp Tyr Phe
                85                  90                  95

Cys Phe His Asp Arg Asp Leu Ser Pro Glu Tyr Gly Ser Leu Lys Asp
            100                 105                 110

Thr Asn Ala Gln Leu Asp Ile Val Thr Asp Tyr Ile Lys Ala Lys Gln
        115                 120                 125

Ala Glu Thr Gly Leu Lys Cys Leu Trp Gly Thr Ala Lys Cys Phe Asp
    130                 135                 140

His Pro Arg Phe Met His Gly Ala Gly Thr Ser Pro Ser Ala Asp Val
145                 150                 155                 160

Phe Ala Phe Ser Ala Ala Gln Ile Lys Lys Ala Leu Glu Ser Thr Val
                165                 170                 175

Lys Leu Gly Gly Thr Gly Tyr Val Phe Trp Gly Gly Arg Glu Gly Tyr
            180                 185                 190

Glu Thr Leu Leu Asn Thr Asn Met Gly Leu Glu Leu Asp Asn Met Ala
        195                 200                 205

Arg Leu Met Lys Met Ala Val Glu Tyr Gly Arg Ser Ile Gly Phe Lys
    210                 215                 220

Gly Asp Phe Tyr Ile Glu Pro Lys Pro Lys Glu Pro Thr Lys His Gln
225                 230                 235                 240

Tyr Asp Phe Asp Thr Ala Thr Val Leu Gly Phe Leu Arg Lys Tyr Gly
                245                 250                 255

Leu Asp Lys Asp Phe Lys Met Asn Ile Glu Ala Asn His Ala Thr Leu
            260                 265                 270

Ala Gln His Thr Phe Gln His Glu Leu Cys Val Ala Arg Thr Asn Gly
        275                 280                 285

Ala Phe Gly Ser Ile Asp Ala Asn Gln Gly Asp Pro Leu Leu Gly Trp
    290                 295                 300
```

-continued

```
Asp Thr Asp Gln Phe Pro Thr Asn Ile Tyr Asp Thr Thr Met Cys Met
305                 310                 315                 320

Tyr Glu Val Ile Lys Ala Gly Gly Phe Thr Asn Gly Gly Leu Asn Phe
                325                 330                 335

Asp Ala Lys Ala Arg Arg Gly Ser Phe Thr Pro Glu Asp Ile Phe Tyr
                340                 345                 350

Ser Tyr Ile Ala Gly Met Asp Ala Phe Ala Leu Gly Tyr Lys Ala Ala
            355                 360                 365

Ser Lys Leu Ile Ala Asp Gly Arg Ile Asp Ser Phe Ile Ser Asp Arg
        370                 375                 380

Tyr Ala Ser Trp Ser Glu Gly Ile Gly Leu Asp Ile Ile Ser Gly Lys
385                 390                 395                 400

Ala Asp Met Ala Ala Leu Glu Lys Tyr Ala Leu Glu Lys Gly Glu Val
                405                 410                 415

Thr Asp Ser Ile Ser Ser Gly Arg Gln Glu Leu Leu Glu Ser Ile Val
                420                 425                 430

Asn Asn Val Ile Phe Asn Leu
            435

<210> SEQ ID NO 12
<211> LENGTH: 440
<212> TYPE: PRT
<213> ORGANISM: Abiotrophia defectiva

<400> SEQUENCE: 12

Met Ser Glu Leu Phe Gln Asn Ile Pro Lys Ile Lys Tyr Glu Gly Ala
1               5                   10                  15

Asn Ser Lys Asn Pro Leu Ala Phe His Tyr Tyr Asp Ala Glu Lys Ile
            20                  25                  30

Val Leu Gly Lys Thr Met Lys Glu His Leu Pro Phe Ala Met Ala Trp
        35                  40                  45

Trp His Asn Leu Cys Ala Ala Gly Thr Asp Met Phe Gly Arg Asp Thr
    50                  55                  60

Ala Asp Lys Ser Phe Gly Leu Glu Lys Gly Ser Met Glu His Ala Lys
65                  70                  75                  80

Ala Lys Val Asp Ala Gly Phe Glu Phe Met Glu Lys Leu Gly Ile Lys
                85                  90                  95

Tyr Phe Cys Phe His Asp Val Asp Leu Val Pro Glu Ala Cys Asp Ile
            100                 105                 110

Lys Glu Thr Asn Ser Arg Leu Asp Glu Ile Ser Asp Tyr Ile Leu Glu
        115                 120                 125

Lys Met Lys Gly Thr Asp Ile Lys Cys Leu Trp Gly Thr Ala Asn Met
130                 135                 140

Phe Ser Asn Pro Arg Phe Val Asn Gly Ala Gly Ser Thr Asn Ser Ala
145                 150                 155                 160

Asp Val Tyr Cys Phe Ala Ala Ala Gln Ile Lys Lys Ala Leu Asp Ile
                165                 170                 175

Thr Val Lys Leu Gly Gly Arg Gly Tyr Val Phe Trp Gly Gly Arg Glu
            180                 185                 190

Gly Tyr Glu Thr Leu Leu Asn Thr Asp Val Lys Phe Glu Gln Glu Asn
        195                 200                 205

Ile Ala Asn Leu Met Lys Met Ala Val Glu Tyr Gly Arg Ser Ile Gly
    210                 215                 220

Phe Lys Gly Asp Phe Tyr Ile Glu Pro Lys Pro Lys Glu Pro Met Lys
```

```
                 225                 230                 235                 240
    His Gln Tyr Asp Phe Asp Ala Ala Thr Ala Ile Gly Phe Leu Arg Gln
                     245                 250                 255

Tyr Gly Leu Asp Lys Asp Phe Lys Leu Asn Ile Glu Ala Asn His Ala
                     260                 265                 270

Thr Leu Ala Gly His Ser Phe Gln His Glu Leu Arg Ile Ser Ser Ile
                     275                 280                 285

Asn Gly Met Leu Gly Ser Val Asp Ala Asn Gln Gly Asp Met Leu Leu
                     290                 295                 300

Gly Trp Asp Thr Asp Glu Phe Pro Phe Asp Val Tyr Asp Thr Thr Met
    305                 310                 315                 320

Cys Met Tyr Glu Val Leu Lys Asn Gly Gly Leu Thr Gly Gly Phe Asn
                     325                 330                 335

Phe Asp Ala Lys Asn Arg Arg Pro Ser Tyr Thr Tyr Glu Asp Met Phe
                     340                 345                 350

Tyr Gly Phe Ile Leu Gly Met Asp Ser Phe Ala Leu Gly Leu Ile Lys
                     355                 360                 365

Ala Ala Lys Leu Ile Glu Glu Gly Thr Leu Asp Asn Phe Ile Lys Glu
                     370                 375                 380

Arg Tyr Lys Ser Phe Glu Ser Glu Ile Gly Lys Lys Ile Arg Ser Lys
    385                 390                 395                 400

Ser Ala Ser Leu Gln Glu Leu Ala Ala Tyr Ala Glu Glu Met Gly Ala
                     405                 410                 415

Pro Ala Met Pro Gly Ser Gly Arg Gln Glu Tyr Leu Gln Ala Ala Leu
                     420                 425                 430

Asn Gln Asn Leu Phe Gly Glu Val
                     435                 440

<210> SEQ ID NO 13
<211> LENGTH: 9901
<212> TYPE: DNA
<213> ORGANISM: artificial sequence
<220> FEATURE:
<223> OTHER INFORMATION: constructed vector containing Ru2 chimeric gene

<400> SEQUENCE: 13
aggccagagg aaaataatat caagtgctgg aaactttttc tcttggaatt tttgcaacat      60
caagtcatag tcaattgaat tgacccaatt tcacatttaa gattttttt ttttcatccg     120 acatacatct gtacactagg aagccctgtt tttctgaagc agcttcaaat atatatattt    180
tttacatatt tattatgatt caatgaacaa tctaattaaa tcgaaaacaa gaaccgaaac    240
gcgaataaat aatttattta gatggtgaca agtgtataag tcctcatcgg gacagctacg    300
atttctcttt cggttttggc tgagctactg gttgctgtga cgcagcggca ttagcgcggc    360
gttatgagct accctcgtgg cctgaaagat ggcgggaata aagcggaact aaaaattact    420
gactgagcca tattgaggtc aatttgtcaa ctcgtcaagt cacgtttggt ggacggcccc    480
tttccaacga atcgtatata ctaacatgcg cgcgcttcct atatacacat atacatatat    540
atatatatat atatgtgtgc gtgtatgtgt acacctgtat ttaatttcct tactcgcggg    600
ttttttcttt ttctcaattc ttggcttcct ctttctcgag cggaccggat cctccgcggt    660
gccggcagat ctatttaaat ggcgcgccga cgtcaggtgg cacttttcgg ggaaatgtgc    720
gcggaacccc tatttgttta ttttttctaaa tacattcaaa tatgtatccg ctcatgagac    780
aataaccctg ataaatgctt caataatatt gaaaaaggaa gagtatgagt attcaacatt    840
```

```
tccgtgtcgc ccttattccc ttttttgcgg cattttgcct tcctgttttt gctcacccag    900
aaacgctggt gaaagtaaaa gatgctgaag atcagttggg tgcacgagtg ggttacatcg    960
aactggatct caacagcggt aagatccttg agagttttcg ccccgaagaa cgttttccaa   1020
tgatgagcac ttttaaagtt ctgctatgtg gcgcggtatt atcccgtatt gacgccgggc   1080
aagagcaact cggtcgccgc atacactatt ctcagaatga cttggttgag tactcaccag   1140
tcacagaaaa gcatcttacg gatggcatga cagtaagaga attatgcagt gctgccataa   1200
ccatgagtga taacactgcg gccaacttac ttctgacaac gatcggagga ccgaaggagc   1260
taaccgcttt tttgcacaac atggggggatc atgtaactcg ccttgatcgt tgggaaccgg   1320
agctgaatga agccatacca aacgacgagc gtgacaccac gatgcctgta gcaatggcaa   1380
caacgttgcg caaactatta actggcgaac tacttactct agcttcccgg caacaattaa   1440
tagactggat ggaggcggat aaagttgcag gaccacttct gcgctcggcc cttccggctg   1500
gctggtttat tgctgataaa tctggagccg gtgagcgtgg gtctcgcggt atcattgcag   1560
cactggggcc agatggtaag ccctcccgta tcgtagttat ctacacgacg gggagtcagg   1620
caactatgga tgaacgaaat agacagatcg ctgagatagg tgcctcactg attaagcatt   1680
ggtaactgtc agaccaagtt tactcatata ctttagat tgatttaaaa cttcattttt   1740
aatttaaaag gatctaggtg aagatccttt ttgataatct catgaccaaa atcccttaac   1800
gtgagttttc gttccactga gcgtcagacc ccgtagaaaa gatcaaagga tcttcttgag   1860
atcctttttt tctgcgcgta atctgctgct tgcaaacaaa aaaaccaccg ctaccagcgg   1920
tggtttgttt gccggatcaa gagctaccaa ctcttttttcc gaaggtaact ggcttcagca   1980
gagcgcagat accaaatact gttcttctag tgtagccgta gttaggccac cacttcaaga   2040
actctgtagc accgcctaca tacctcgctc tgctaatcct gttaccagtg gctgctgcca   2100
gtggcgataa gtcgtgtctt accgggttgg actcaagacg atagttaccg gataaggcgc   2160
agcggtcggg ctgaacgggg ggttcgtgca cacagcccag cttggagcga acgacctaca   2220
ccgaactgag atacctacag cgtgagctat gagaaagcgc cacgcttccc gaagggagaa   2280
aggcggacag gtatccggta agcggcaggg tcggaacagg agagcgcacg agggagcttc   2340 caggggggaaa cgcctggtat ctttatagtc ctgtcgggtt tcgccacctc tgacttgagc   2400
gtcgattttt gtgatgctcg tcaggggggc ggagcctatg gaaaaacgcc agcaacgcgg   2460 ccttttttacg gttcctggcc ttttgctggc cttttgctca catgttcttt cctgcgttat   2520
cccctgattc tgtggataac cgtattaccg cctttgagtg agctgatacc gctcgccgca   2580
gccgaacgac cgagcgcagc gagtcagtga gcgaggaagc ggaagagcgc ccaatacgca   2640
aaccgcctct ccccgcgcgt tggccgattc attaatgcag ctggcacgac aggtttcccg   2700
actggaaagc gggcagtgag cgcaacgcaa ttaatgtgag ttagctcact cattaggcac   2760
cccaggcttt acactttatg cttccggctc gtatgttgtg tggaattgtg agcggataac   2820
aatttcacac aggaaacagc tatgaccatg attacgccaa gcttttctt tccaattttt   2880 tttttttcgt cattataaaa atcattacga ccgagattcc cgggtaataa ctgatataat   2940
taaattgaag ctctaatttg tgagtttagt atacatgcat ttacttataa tacagttttt   3000
tagttttgct ggccgcatct tctcaaatat gcttcccagc ctgcttttct gtaacgttca   3060
ccctctacct tagcatccct tccctttgca aatagtcctc ttccaacaat aataatgtca   3120
gatcctgtag agaccacatc atccacggtt ctatactgtt gacccaatgc gtctcccttg   3180
tcatctaaac ccacaccggg tgtcataatc aaccaatcgt aaccttcatc tcttccaccc   3240
```

```
atgtctcttt gagcaataaa gccgataaca aaatctttgt cgctcttcgc aatgtcaaca    3300
gtacccttag tatattctcc agtagatagg gagcccttgc atgacaattc tgctaacatc    3360
aaaaggcctc taggttcctt tgttacttct tctgccgcct gcttcaaacc gctaacaata    3420
cctgggccca ccacaccgtg tgcattcgta atgtctgccc attctgctat tctgtataca    3480
cccgcagagt actgcaattt gactgtatta ccaatgtcag caaattttct gtcttcgaag    3540
agtaaaaaat tgtacttggc ggataatgcc tttagcggct taactgtgcc ctccatggaa    3600
aaatcagtca agatatccac atgtgttttt agtaaacaaa ttttgggacc taatgcttca    3660
actaactcca gtaattcctt ggtggtacga acatccaatg aagcacacaa gtttgtttgc    3720
ttttcgtgca tgatattaaa tagcttggca gcaacaggac taggatgagt agcagcacgt    3780
tccttatatg tagctttcga catgattat cttcgtttcc tgcaggtttt tgttctgtgc    3840
agttgggtta agaatactgg gcaatttcat gtttcttcaa cactacatat gcgtatatat    3900
accaatctaa gtctgtgctc cttccttcgt tcttccttct gttcggagat taccgaatca    3960 aaaaatttc aaggaaaccg aaatcaaaaa aaagaataaa aaaaaatga tgaattgaaa    4020 agcttgcatg cctgcaggtc gactctagta tactccgtct actgtacgat acacttccgc    4080
tcaggtcctt gtcctttaac gaggccttac cactcttttg ttactctatt gatccagctc    4140
agcaaaggca gtgtgatcta agattctatc ttcgcgatgt agtaaaacta gctagaccga    4200
gaaagagact agaaatgcaa aaggcacttc tacaatggct gccatcatta ttatccgatg    4260
tgacgctgca ttttttttt tttttttttt tttttttttt tttttttttt tttttttttt    4320
ttgtacaaat atcataaaaa aagagaatct ttttaagcaa ggattttctt aacttcttcg    4380
gcgacagcat caccgacttc ggtggtactg ttggaaccac ctaaatcacc agttctgata    4440
cctgcatcca aaaccttttt aactgcatct tcaatggctt taccttcttc aggcaagttc    4500
aatgacaatt tcaacatcat tgcagcagac aagatagtgg cgatagggtt gaccttattc    4560
tttggcaaat ctggagcgga accatggcat ggttcgtaca aaccaaatgc ggtgttcttg    4620
tctggcaaag aggccaagga cgcagatggc aacaaaccca aggagcctgg gataacggag    4680
gcttcatcgg agatgatatc accaaacatg ttgctggtga ttataatacc atttaggtgg    4740
gttgggttct taactaggat catggcggca gaatcaatca attgatgttg aactttcaat    4800
gtagggaatt cgttcttgat ggtttcctcc acagttttc tccataatct tgaagaggcc    4860
aaaacattag ctttatccaa ggaccaaata ggcaatggtg gctcatgttg tagggccatg    4920
aaagcggcca ttcttgtgat tctttgcact tctggaacgg tgtattgttc actatcccaa    4980
gcgacaccat caccatcgtc ttcctttctc ttaccaaagt aaatacctcc cactaattct    5040
ctaacaacaa cgaagtcagt acctttagca aattgtggct tgattggaga taagtctaaa    5100
agagagtcgg atgcaaagtt acatggtctt aagttggcgt acaattgaag ttctttacgg    5160
atttttagta aaccttgttc aggtctaaca ctaccggtac cccatttagg accacccaca    5220
gcacctaaca aaacggcatc agccttcttg gaggcttcca gcgcctcatc tggaagtgga    5280
acacctgtag catcgatagc agcaccacca attaaatgat tttcgaaatc gaacttgaca    5340
ttggaacgaa catcagaaat agctttaaga accttaatgg cttcggctgt gatttcttga    5400
ccaacgtggt cacctggcaa aacgacgatc ttcttagggg cagacattac aatggtatat    5460
ccttgaaata tatataaaaa aaaaaaaaaa aaaaaaaaaa aaaatgcag cttctcaatg    5520 atattcgaat acgctttgag gagatacagc ctaatatccg acaaactgtt ttacagattt    5580
```

```
acgatcgtac ttgttaccca tcattgaatt ttgaacatcc gaacctggga gttttccctg   5640
aaacagatag tatatttgaa cctgtataat aatatatagt ctagcgcttt acggaagaca   5700
atgtatgtat ttcggttcct ggagaaacta ttgcatctat tgcataggta atcttgcacg   5760
tcgcatcccc ggttcatttt ctgcgtttcc atcttgcact tcaatagcat atctttgtta   5820
acgaagcatc tgtgcttcat tttgtagaac aaaaatgcaa cgcgagagcg ctaattttc    5880 aaacaaagaa tctgagctgc attttacag aacagaaatg caacgcgaaa gcgctatttt    5940
accaacgaag aatctgtgct tcattttgt aaaacaaaa tgcaacgcga gagcgctaat     6000
ttttcaaaca aagaatctga gctgcatttt tacagaacag aaatgcaacg cgagagcgct   6060
attttaccaa caaagaatct atacttcttt tttgttctac aaaaatgcat cccgagagcg   6120
ctatttttct aacaaagcat cttagattac ttttttctc ctttgtgcgc tctataatgc    6180
agtctcttga taactttttg cactgtaggt ccgttaaggt tagaagaagg ctactttggt   6240
gtctattttc tcttccataa aaaaagcctg actccacttc ccgcgtttac tgattactag   6300
cgaagctgcg ggtgcatttt ttcaagataa aggcatcccc gattatattc tataccgatg   6360
tggattgcgc atactttgtg aacagaaagt gatagcgttg atgattcttc attggtcaga   6420
aaattatgaa cggtttcttc tattttgtct ctatatacta cgtataggaa atgtttacat   6480
tttcgtattg ttttcgattc actctatgaa tagttcttac tacaattttt ttgtctaaag   6540
agtaatacta gagataaaca taaaaaatgt agaggtcgag tttagatgca agttcaagga   6600
gcgaaaggtg gatgggtagg ttatataggg atatagcaca gagatatata gcaaagagat   6660
acttttgagc aatgtttgtg gaagcggtat tcgcaatatt ttagtagctc gttacagtcc   6720
ggtgcgtttt tggttttttg aaagtgcgtc ttcagagcgc ttttggtttt caaaagcgct   6780
ctgaagttcc tatactttct agagaatagg aacttcggaa taggaacttc aaagcgtttc   6840
cgaaaacgag cgcttccgaa aatgcaacgc gagctgcgca catacagctc actgttcacg   6900
tcgcacctat atctgcgtgt tgcctgtata tatatataca tgagaagaac ggcatagtgc   6960
gtgtttatgc ttaaatgcgt acttatatgc gtctatttat gtaggatgaa aggtagtcta   7020
gtacctcctg tgatattatc ccattccatg cggggtatcg tatgcttcct tcagcactac   7080
cctttagctg ttctatatgc tgccactcct caattggatt agtctcatcc ttcaatgcta   7140
tcatttcctt tgatattgga tcatatgcat agtaccgaga aactagagga tctcccatta   7200
ccgacatttg ggcgctatac gtgcatatgt tcatgtatgt atctgtattt aaaacacttt   7260
tgtattattt ttcctcatat atgtgtatag gtttatacgg atgatttaat tattacttca   7320 ccaccctta tttcaggctg atatcttagc cttgttacta gtcaccggtg gcggccgcac    7380
ctggtaaaac ctctagtgga gtagtagatg taatcaatga agcggaagcc aaaagaccag   7440
agtagaggcc tatagaagaa actgcgatac cttttgtgat ggctaaacaa acagacatct   7500
ttttatatgt tttacttct gtatatcgtg aagtagtaag tgataagcga atttggctaa    7560
gaacgttgta agtgaacaag ggacctcttt tgcctttcaa aaaaggatta aatggagtta   7620
atcattgaga tttagttttc gttagattct gtatccctaa ataactccct tacccgacgg   7680
gaaggcacaa aagacttgaa taatagcaaa cggccagtag ccaagaccaa ataatactag   7740
agttaactga tggtcttaaa caggcattac gtggtgaact ccaagaccaa tatacaaaat   7800
atcgataagt tattccttgcc caccaattta aggagcctac atcaggacag tagtaccatt   7860
cctcagagaa gaggtataca taacaagaaa atcgcgtgaa caccttatat aacttagccc   7920
gttattgagc taaaaaacct tgcaaaattt cctatgaata agaatacttc agacgtgata   7980
```

```
aaaatttact ttctaactct tctcacgctg ccoctatctg ttcttccgct ctaccgtgag    8040
aaataaagca tcgagtacgg cagttcgctg tcactgaact aaaacaataa ggctagttcg    8100
aatgatgaac ttgcttgctg tcaaacttct gagttgccgc tgatgtgaca ctgtgacaat    8160
aaattcaaac cggttatagc ggtctcctcc ggtaccggtt ctgccacctc caatagagct    8220
cagtaggagt cagaacctct gcggtggctg tcagtgactc atccgcgttt cgtaagttgt    8280
gcgcgtgcac atttcgcccg ttcccgctca tcttgcagca ggcggaaatt ttcatcacgc    8340
tgtaggacgc aaaaaaaaaa taattaatcg tacaagaatc ttggaaaaaa aattgaaaaa    8400
ttttgtataa aagggatgac ctaacttgac tcaatggctt ttacacccag tattttccct    8460
ttccttgttt gttacaatta tagaagcaag acaaaaacat atagacaacc tattcctagg    8520
agttatattt ttttacccta ccagcaatat aagtaaaaaa ctgtttaaac agtatgggtg    8580
aaatcttctc taacatccca gtcatcaagt acgaaggtcc agactctaag aacccattgg    8640
ctttcaagta ctacgatcca gaaagagtca tcttgggtaa aaagatgaag gaacacttgc    8700
cattcgctat ggcttggtgg cacaacttgt gtgctaacgg tgttgacatg ttcggtagag    8760
gtactatcga taagttgttc ggtgctgctg aagctggtac tatggaacac gctaaggcta    8820
aggttgacgc tggtatcgag ttcatgcaaa agttgggtat cgaatactac tgtttccacg    8880
acgttgattt ggtcccagaa gctgacgata tcaacgaaac caacagaaga ttggacgaat    8940
tgactgatta cttgaaggaa aagaccgctg gtactaacat caagtgtttg tggggtactg    9000
ctaacatgtt ctctaaccca agattcatga acggtgctgg ttccactaac gacgttgatg    9060
tctactgttt cgctgctgct caagttaaga aggctatcga aatgaccgtc aagttgggtg    9120
gtagaggtta cgttttctgg ggtggtagag aaggttacga aaccttgttg aacactaagg    9180
tccaaatgga attggaaaac atcgctaact tgatgaagat ggctagagac tacggtagat    9240
ctatcggttt caagggtact ttcttgatcg aaccaaagcc aaaggaacca atgaagcacc    9300
aatacgacta cgatgctgct actgctatcg gtttcttgag acaatacggt ttggaccaag    9360
atttcaagat gaacatcgaa gctaaccacg ctaccttggc tggtcacact ttccaacacg    9420
aattgagaat ctctagaatc aacggtatgt tgggttccat cgacgctaac caaggtgaca    9480
tcatgttggg ttgggacacc gattgtttcc catctaacgt ttacgacacc actttggcta    9540
tgtacgaaat cgttagaaac ggtggtttgc agtcggtat caacttcgac tctaagaaca    9600
gaagaccatc caacacttac gaagacatgt ccacgctttt catcttgggt atggactctt    9660
tcgctttcgg tttgatcaag gctgctcaaa tcatcgaaga cggtagaatc gaaggtttca    9720
ccgaaaagaa gtacgaatcc ttcaacactg aattgggtca aagatcaga aagggtgaag    9780 ctactttgga agaattggct gctcacgctg ctgacttgaa ggctccaaag gttccagtct    9840
ctggtagaca agaatacttg gaaggtgttt tgaacaacat catcttgtcc tgaggccctg    9900
c                                                                    9901

<210> SEQ ID NO 14
<211> LENGTH: 16404
<212> TYPE: DNA
<213> ORGANISM: Artificial sequence
<220> FEATURE:
<223> OTHER INFORMATION: constructed plasmid

<400> SEQUENCE: 14
gatccacgat cgcattgcgg attacgtatt ctaatgttca gtaccgttcg tataatgtat      60
```

```
gctatacgaa gttatgcaga ttgtactgag agtgcaccat accacagctt tcaattcaa      120 ttcatcattt tttttttatt cttttttttg atttcggttt ctttgaaatt tttttgattc      180
ggtaatctcc gaacagaagg aagaacgaag gaaggagcac agacttagat tggtatatat      240
acgcatatgt agtgttgaag aaacatgaaa ttgcccagta ttcttaaccc aactgcacag      300
aacaaaaacc tgcaggaaac gaagataaat catgtcgaaa gctacatata aggaacgtgc      360
tgctactcat cctagtcctg ttgctgccaa gctatttaat atcatgcacg aaaagcaaac      420
aaacttgtgt gcttcattgg atgttcgtac caccaaggaa ttactggagt tagttgaagc      480
attaggtccc aaaatttgtt tactaaaaac acatgtggat atcttgactg attttccat       540 ggagggcaca gttaagccgc taaaggcatt atccgccaag tacaatttt tactcttcga       600 agacagaaaa tttgctgaca ttggtaatac agtcaaattg cagtactctg cgggtgtata      660
cagaatagca gaatgggcag acattacgaa tgcacacggt gtggtgggcc caggtattgt      720
tagcggtttg aagcaggcgg cagaagaagt aacaaaggaa cctagaggcc ttttgatgtt      780
agcagaattg tcatgcaagg gctccctatc tactggagaa tatactaagg gtactgttga      840
cattgcgaag agcgacaaag attttgttat cggctttatt gctcaaagag acatgggtgg      900
aagagatgaa ggttacgatt ggttgattat gacacccggt gtgggtttag atgacaaggg      960
agacgcattg ggtcaacagt atagaaccgt ggatgatgtg gtctctacag gatctgacat     1020
tattattgtt ggaagaggac tatttgcaaa gggaagggat gctaaggtag agggtgaacg     1080
ttacagaaaa gcaggctggg aagcatattt gagaagatgc ggccagcaaa actaaaaaac     1140
tgtattataa gtaaatgcat gtatactaaa ctcacaaatt agagcttcaa tttaattata     1200
tcagttatta ccctatgcgg tgtgaaatac cgcacagatg cgtaaggaga aataccgca      1260 tcaggaaatt gtaaacgtta atattttgtt aaaattcgcg ttaaattttt gttaaatcag     1320
ctcatttttt aaccaatagg ccgaaatcgg caaaatccct tataaatcaa agaatagac      1380 cgagataggg ttgagtgttg ttccagtttg aacaagagt ccactattaa agaacgtgga      1440
ctccaacgtc aaagggcgaa aaaccgtcta tcagggcgat ggcccactac gtgaaccatc     1500
accctaatca agataacttc gtataatgta tgctatacga acggtacccg ccaactctgt     1560
tcgagaatga tgtaatcaag aaggtctcac aaaaccatcc aggcagtacc acttcccaag     1620
tattgcttag atgggcaact cagagaggca ttgccgtcat tccaaaatct tccaagaagg     1680
aaaggttact tggcaaccta gaaatcgaaa aaagttcac tttaacggag caagaattga      1740
aggatatttc tgcactaaat gccaacatca gatttaatga tccatggacc tggttggatg     1800
gtaaattccc cacttttgcc tgatccagcc agtaaaatcc atactcaacg acgatatgaa     1860
caaatttccc tcattccgat gctgtatatg tgtataaatt tttacatgct cttctgttta     1920
gacacagaac agctttaaat aaaatgttgg atatacttt tctgcctgtg gtgtcatcca      1980
cgcttttaat tcatctcttg tatggttgac aatttggcta ttttttaaca gaacccaacg     2040
gtaattgaaa ttaaaaggga aacgagtggg ggcgatgagt gagtgatacg gcgcctgatg     2100
cggtattttc tccttacgca tctgtgcggt atttcacacc gcatatggtg cactctcagt     2160
acaatctgct ctgatgccgc atagttaagc cagccccgac acccgccaac acccgctgac     2220
gcgccctgac gggcttgtct gctcccggca tccgcttaca gacaagctgt gaccgtctcc     2280
gggagctgca tgtgtcagag gttttcaccg tcatcaccga aacgcgcgag acgaaagggc     2340
ctcgtgatac gcctattttt ataggttaat gtcatgataa taatggtttc ttagacgtca     2400
ggtggcactt ttcggggaaa tgtgcgcgga acccctattt gtttattttt ctaaatacat     2460
```

```
tcaaatatgt atccgctcat gagacaataa ccctgataaa tgcttcaata atattgaaaa    2520
aggaagagta tgagtattca acatttccgt gtcgcccttz ttcccttttt tgcggcattt    2580
tgccttcctg tttttgctca cccagaaacg ctggtgaaag taaaagatgc tgaagatcag    2640
ttgggtgcac gagtgggtta catcgaactg gatctcaaca gcggtaagat ccttgagagt    2700
tttcgccccg aagaacgttt tccaatgatg agcacttttz aagttctgct atgtggcgcg    2760
gtattatccc gtattgacgc cgggcaagag caactcggtc gccgcataca ctattctcag    2820
aatgacttgg ttgagtactc accagtcaca gaaaagcatc ttacggatgg catgacagta    2880
agagaattat gcagtgctgc cataaccatg agtgataaca ctgcggccaa cttacttctg    2940
acaacgatcg gaggaccgaa ggagctaacc gcttttttgc acaacatggg ggatcatgta    3000
actcgccttg atcgttggga accggagctg aatgaagcca taccaaacga cgagcgtgac    3060
accacgatgc ctgtagcaat ggcaacaacg ttgcgcaaac tattaactgg cgaactactt    3120
actctagctt cccggcaaca attaatagac tggatggagg cggataaagt tgcaggacca    3180
cttctgcgct cggcccttcc ggctggctgg tttattgctg ataaatctgg agccggtgag    3240
cgtgggtctc gcggtatcat tgcagcactg gggccagatg gtaagccctc ccgtatcgta    3300
gttatctaca cgacggggag tcaggcaact atggatgaac gaaatagaca gatcgctgag    3360
ataggtgcct cactgattaa gcattggtaa ctgtcagacc aagtttactc atatatactt    3420
tagattgatt taaaacttca ttttttaattt aaaaggatct aggtgaagat cctttttgat    3480
aatctcatga ccaaaatccc ttaacgtgag ttttcgttcc actgagcgtc agaccccgta    3540
gaaaagatca aggatcttc ttgagatcct ttttttctgc gcgtaatctg ctgcttgcaa    3600
acaaaaaaac caccgctacc agcggtggtt tgtttgccgg atcaagagct accaactctt    3660
tttccgaagg taactggctt cagcagagcg cagataccaa atactgtcct tctagtgtag    3720
ccgtagttag gccaccactt caagaactct gtagcaccgc ctacatacct cgctctgcta    3780
atcctgttac cagtggctgc tgccagtggc gataagtcgt gtcttaccgg gttggactca    3840
agacgatagt taccggataa ggcgcagcgg tcgggctgaa cggggggttc gtgcacacag    3900
cccagcttgg agcgaacgac ctacaccgaa ctgagatacc tacagcgtga gctatgagaa    3960
agcgccacgc ttcccgaagg gagaaaggcg gacaggtatc cggtaagcgg cagggtcgga    4020
acaggagagc gcacgaggga gcttccaggg ggaaacgcct ggtatcttta tagtcctgtc    4080
gggtttcgcc acctctgact tgagcgtcga ttttttgtgat gctcgtcagg ggggcggagc    4140
ctatggaaaa acgccagcaa cgcggccttt ttacggttcc tggccttttg ctggccttttg   4200
gctcacatgt tctttcctgc gttatcccct gattctgtgg ataaccgtat taccgccttt    4260
gagtgagctg ataccgctcg ccgcagccga acgaccgagc gcagcgagtc agtgagcgag    4320
gaagcggaag agcgcccaat acgcaaaccg cctctccccg cgcgttggcc gattcattaa    4380
tgcagctggc acgacaggtt tcccgactgg aaagcgggca gtgagcgcaa cgcaattaat    4440
gtgagttagc tcactcatta ggcaccccag gctttacact ttatgcttcc ggctcgtatg    4500
ttgtgtggaa ttgtgagcgg ataacaattt cacacaggaa acagctatga ccatgattag    4560
gcgcctactt ctagggggcc tatcaagtaa attactcctg gtacactgaa gtatataagg    4620
gatatagaag caaatagttg tcagtgcaat ccttcaagac gattgggaaa atactgtaat    4680
ataaatcgta aaggaaaatt ggaaatttttt taaagatgtc ttcactggtt actcttaata    4740
acggtctgaa aatgccccta gtcggcttag ggtgctggaa aattgacaaa aaagtctgtg    4800
```

```
cgaatcaaat ttatgaagct atcaaattag ctaccgtttt attcgatggt gcttgcgact    4860
acggcaacga aaaggaagtt ggtgaaggta tcaggaaagc catctccgaa ggtcttgttt    4920
ctagaaagga tatatttgtt gtttcaaagt tatggaacaa ttttcaccat cctgatcatg    4980
taaaattagc tttaaagaag accttaagcg atatgggact tgattattta gacctgtatt    5040
atattcactt cccaatcgcc ttcaaatatg ttccatttga agagaaatac cctccaggat    5100
tctatacggg cgcagaagga ttctatacgg gcgcagaact agtgatctcg aggttccaga    5160
gctcggatcc accacaggtg ttgtcctctg aggacataaa atacacaccg agattcatca    5220
actcattgct ggagttagca tatctacaat tgggtgaaat ggggagcgat ttgcaggcat    5280
ttgctcggca tgccggtaga ggtgtggtca ataagagcga cctcatgcta tacctgagaa    5340
agcaacctga cctacaggaa agagttactc aagaataaga attttcgttt taaaacctaa    5400
gagtcacttt aaaatttgta tacacttatt ttttttataa cttatttaat aataaaaatc    5460
ataaatcata agaaattcgc ttactcatcc cgggttagat gagagtcttt tccagttcgc    5520 ttaagggac aatcttggaa ttatagcgat cccaattttc attatccaca tcggatatgc    5580
tttccattac atgccatgga aaattgtcat tcagaaattt atcaaaagga actgcaattt    5640
tattagagtc atataacaat gaccacatgg ccttataaca accaccaagg gcacatgagt    5700
ttggtgtttc tagcctaaaa ttacccttttg tagcaccaat gacttgagca aacttcttca    5760
caatagcatc gtttttagaa gccccaccta caaaaaaagt cctttctggc cttttattta    5820
ggtagtcccg cagcggagat tcatcgtaat caaacttcac gattgtatct tcgttcagtc    5880
tctgttgtga gcttgcgttt gaatccgaaa gcagggggaga tattcttacc ctgcaactta    5940
aagcctgtga ttctacaata tttttggcat cgtgcctctt gtctttgaac ttggccacct    6000
ctctttcaat catacccgtt tttggattga agataaccct tttgtttatg gcttttacgc    6060
taggaacgat ctccccccaga ggaaaatata cacctaattc attttcacta ctttctgagt    6120
catctagcac agcttgatta aaagagtcc aatcgttagt cttctcataa ttattttccc    6180
gttctttgtt taactcgtct cttatcctct cccttgccaa agaaccatta caataacaaa    6240
tcatacccat ataatggttt ggcagagttg gatgaatgaa aagatgatag ttcggagagg    6300
ggtgatactt atcggtgacc agaagaactg tagtacttgt tcctagggaa acgagaacgt    6360
cattcttccg caggggtaaa gaacatatag tggctaaatt atccccagtc atgggagaga    6420
ccttgcagtt tgtattgaaa ccgtacttct caataaaata tttacagatg gtacccgcta    6480
tcaaattttt catgggtgct ctcattaatt tttgtctgat agtttatcc ttagaagaac    6540 tatcaattag atgtagtagc tcatcactga attttctttc acgtatatca taaggttca    6600 taccacaggc atctgcctcc tctaattcaa caagatggcc cactaagata gaagtcaaaa    6660
aattagacac taaagaaatg gtctttgttt tttcgtaagc ttctggttct aattgtgcaa    6720
ttttcagaat ttgaggacca gtaaatctaa aatgggctct ggaccctgtt aattgagcca    6780 tttttttcagg cccacctatg cactcttcaa actcttgaca ttgctttgca gtactgtggt    6840
cttgccaatt gggggcggtt tgccttgcaa atgctacaga gctcacgtag tgcaataaat    6900 cttttttccgg tttcttattc aattgctcta acagagattc ggcttgggag gaccagtaga    6960
cagacccgtg ctgctggcag gaccctgaga cggccataac tttgttcaat ggaaatttag    7020
cctcgcgata tttcgagaga accagatcta gagcctctaa ccacatggct acgggacatt    7080
cgatagtgtc gccgtgtata tagacaccct tctttgtgtg ataatgcgga agatcctttt    7140
caaattccac tgtttctgaa tggacaattt ttaggtcctg gttaatggcg agacatttca    7200
```

```
gttgttgggt cgaaagatca aacccaagat agtatgagtc taaagacatt gtgttggaaa   7260
cctctcttgt ctgtctctga attactgaac acaacatact agtcgtacgg ttttattttt   7320
tacttatatt gctggtaggg taaaaaaata taactcctag gaataggttg tctatatgtt   7380
tttgtcttgc ttctataatt gtaacaaaca aggaaaggga aaatactggg tgtaaaagcc   7440
attgagtcaa gttaggtcat ccctttata caaaattttt caattttttt tccaagattc    7500
ttgtacgatt aattattttt ttttgcgtc ctacagcgtg atgaaaattt ccgcctgctg    7560
caagatgagc gggaacgggc gaaatgtgca cgcgcacaac ttacgaaacg cggatgagtc   7620
actgacagcc accgcagagg ttctgactcc tactgagctc tattggaggt ggcagaaccg   7680
gtaccggagg agaccgctat aaccggttg aatttattgt cacagtgtca catcagcggc    7740
aactcagaag tttgacagca agcaagttca tcattcgaac tagccttatt gttttagttc   7800
agtgacagcg aactgccgta ctcgatgctt tatttctcac ggtagagcgg aagaacagat   7860
aggggcagcg tgagaagagt tagaaagtaa attttatca cgtctgaagt attcttattc     7920
ataggaaatt ttgcaaggtt ttttagctca ataacgggct aagttatata aggtgttcac   7980
gcgattttct tgttatgtat acctcttctg gcgcgcctct ttttattaac cttaattttt   8040
attttagatt cctgacttca actcaagacg cacagatatt ataacatctg cataataggc   8100
atttgcaaga attactcgtg agtaaggaaa gagtgaggaa ctatcgcata cctgcattta   8160
aagatgccga tttgggcgcg aatcctttat tttggcttca ccctcatact attatcaggg   8220
ccagaaaaag gaagtgtttc cctccttctt gaattgatgt taccctcata aagcacgtgg   8280
cctcttatcg agaaagaaat taccgtcgct cgtgatttgt ttgcaaaaag aacaaaactg   8340
aaaaaaccca gacacgctcg acttcctgtc ttcctattga ttgcagcttc caatttcgtc    8400
acacaacaag gtcctagcga cggctcacag gttttgtaac aagcaatcga aggttctgga   8460
atggcgggaa agggtttagt accacatgct atgatgccca ctgtgatctc cagagcaaag   8520
ttcgttcgat cgtactgtta ctctctctct ttcaaacaga attgtccgaa tcgtgtgaca   8580
acaacagcct gttctcacac actctttct tctaaccaag ggggtggttt agtttagtag    8640
aacctcgtga aacttacatt tacatatata taaacttgca taaattggtc aatgcaagaa   8700
atacatattt ggtcttttct aattcgtagt ttttcaagtt cttagatgct ttcttttct    8760 cttttttaca gatcatcaag gaagtaatta tctactttt acaacaaata taaaacacgt    8820
acgactagta tgactcaatt cactgacatt gataagttgg ccgtctccac cataagaatt   8880
ttggctgtgg acaccgtatc caaggccaac tcaggtcacc caggtgctcc attgggtatg   8940
gcaccagctg cacacgttct atggagtcaa atgcgcatga acccaaccaa cccagactgg   9000
atcaacagag atagatttgt cttgtctaac ggtcacgcgg tcgctttgtt gtattctatg   9060
ctacatttga ctggttacga tctgtctatt gaagacttga aacagttcag acagttgggt   9120
tccagaacac caggtcatcc tgaatttgag ttgccaggtg ttgaagttac taccggtcca   9180
ttaggtcaag gtatctccaa cgctgttggt atggccatgg ctcaagctaa cctggctgcc   9240
acttacaaca agccgggctt taccttgtct gacaactaca cctatgttt cttgggtgac   9300 ggttgtttgc aagaaggtat ttcttcagaa gcttcctcct ggctggtca tttgaaattg    9360 ggtaacttga ttgccatcta cgatgacaac aagatcacta tcgatggtgc taccagtatc   9420
tcattcgatg aagatgttgc taagagatac gaagcctacg gtgggaagt tttgtacgta    9480 gaaaatggta acgaagatct agccggtatt gccaaggcta ttgctcaagc taagttatcc   9540
```

```
aaggacaaac caactttgat caaaatgacc acaaccattg gttacggttc cttgcatgcc    9600
ggctctcact ctgtgcacgg tgccccattg aaagcagatg atgttaaaca actaaagagc    9660
aaattcggtt tcaacccaga caagtccttt gttgttccac aagaagttta cgaccactac    9720
caaaagacaa ttttaaagcc aggtgtcgaa gccaacaaca agtggaacaa gttgttcagc    9780
gaataccaaa agaaattccc agaattaggt gctgaattgg ctagaagatt gagcggccaa    9840
ctacccgcaa attgggaatc taagttgcca acttacaccg ccaaggactc tgccgtggcc    9900
actagaaaat tatcagaaac tgttcttgag gatgtttaca atcaattgcc agagttgatt    9960
ggtggttctg ccgatttaac accttctaac ttgaccagat ggaaggaagc ccttgacttc   10020
caacctcctt cttccggttc aggtaactac tctggtagat acattaggta cggtattaga   10080
gaacacgcta tgggtgccat aatgaacggt atttcagctt tcggtgccaa ctacaaacca   10140
tacggtggta ctttcttgaa cttcgtttct tatgctgctg gtgccgttag attgtccgct   10200
ttgtctggcc acccagttat ttgggttgct acacatgact ctatcggtgt cggtgaagat   10260
ggtccaacac atcaacctat tgaaacttta gcacacttca gatccctacc aaacattcaa   10320
gtttggagac cagctgatgg taacgaagtt tctgccgcct acaagaactc tttagaatcc   10380
aagcatactc caagtatcat tgctttgtcc agacaaaact tgccacaatt ggaaggtagc   10440
tctattgaaa gcgcttctaa gggtggttac gtactacaag atgttgctaa cccagatatt   10500
attttagtgg ctactggttc cgaagtgtct ttgagtgttg aagctgctaa gactttggcc   10560
gcaaagaaca tcaaggctcg tgttgtttct ctaccagatt tcttcacttt tgacaaacaa   10620
cccctagaat acagactatc agtcttacca gacaacgttc aatcatgtc tgttgaagtt    10680
ttggctacca catgttgggg caaatacgct catcaatcct tcggtattga cagatttggt   10740
gcctccggta aggcaccaga agtcttcaag ttcttcggtt tcaccccaga aggtgttgct   10800
gaaagagctc aaaagaccat tgcattctat aagggtgaca agctaatttc tcctttgaaa   10860
aaagcttttct aaattctgat cgtagatcat cagatttgat atgatattat ttgtgaaaaa   10920
atgaaataaa actttataca acttaaatac aactttttttt ataaacgatt aagcaaaaaa   10980
atagtttcaa acttttaaca atattccaaa cactcagtcc ttttccttct tatattatag   11040
gtgtacgtat tatagaaaaa tttcaatgat tactttttct ttcttttttcc ttgtaccagc   11100
acatggccga gctgaatgt taaacccttc gagagaatca caccattcaa gtataaagcc    11160
aataaagaat ataactccta aaaggctaat tgaaaccctg tgattttttgc ccgggtttaa   11220
ggcgcgccct ttatcattat caatactgcc atttcaaaga atacgtaaat aattaatagt   11280
agtgattttc ctaactttat ttagtcaaaa aattagcctt ttaattctgc tgtaacccgt   11340
acatgcccaa aataggggc gggttacaca gaatatataa catcgtaggt gtctgggtga    11400
acagtttatt cctggcatcc actaaatata atggagcccg cttttttaagc tggcatccag   11460
aaaaaaaaag aatcccagca ccaaaatatt gttttcttca ccaaccatca gttcataggt   11520
ccattctctt agcgcaacta cagagaacag gggcacaaac aggcaaaaaa cgggcacaac   11580
ctcaatggag tgatgcaacc tgcctggagt aaatgatgac acaaggcaat tgacccacgc   11640
atgtatctat ctcattttct tacaccttct attaccttct gctctctctg atttggaaaa   11700
agctgaaaaa aaaggttgaa accagttccc tgaaattatt cccctacttg actaataagt   11760
atataaagac ggtaggtatt gattgtaatt ctgtaaatct atttcttaaa cttcttaaat   11820
tctacttttta tagttagtct tttttttagt tttaaaacac caagaactta gtttcgaata   11880
aacacacata aacaaacacc actagcatgg ctgccggtgt cccaaaaatt gatgcgttag   11940
```

```
aatctttggg caatcctttg gaggatgcca agagagctgc agcatacaga gcagttgatg    12000
aaaatttaaa atttgatgat cacaaaatta ttggaattgg tagtggtagc acagtggttt    12060
atgttgccga agaattggaa caatatttgc atgaccctaa attttatgaa gtagcgtcta    12120
aattcatttg cattccaaca ggattccaat caagaaactt gattttggat aacaagttgc    12180
aattaggctc cattgaacag tatcctcgca ttgatatagc gtttgacggt gctgatgaag    12240
tggatgagaa tttacaatta attaaaggtg gtggtgcttg tctatttcaa gaaaaattgg    12300
ttagtactag tgctaaaacc ttcattgtcg ttgctgattc aagaaaaaag tcaccaaaac    12360
atttaggtaa gaactggagg caaggtgttc ccattgaaat tgtaccttcc tcatacgtga    12420
gggtcaagaa tgatctatta gaacaattgc atgctgaaaa agttgacatc agacaaggag    12480
gttctgctaa agcaggtcct gttgtaactg acaataataa cttcattatc gatgcggatt    12540
tcggtgaaat ttccgatcca agaaaattgc atagagaaat caaactgtta gtgggcgtgg    12600
tggaaacagg tttattcatc gacaacgctt caaaagccta cttcggtaat tctgacggta    12660
gtgttgaagt taccgaaaag tgagcggccg cgtgaattta ctttaaatct tgcatttaaa    12720 taaatttttct ttttatagct ttatgactta gtttcaattt atatactatt ttaatgacat    12780
tttcgattca ttgattgaaa gctttgtgtt ttttcttgat gcgctattgc attgttcttg    12840 tcttttttcgc cacatgtaat atctgtagta gatacctgat acattgtgga tgctgagtga    12900
aattttagtt aataatggag gcgctcttaa taattttggg gatattggct ttttttttta    12960
aagtttacaa atgaatttttt tccgccagga taacgattct gaagttactc ttagcgttcc    13020
tatcggtaca gccatcaaat catgcctata aatcatgcct atatttgcgt gcagtcagta    13080
tcatctacat gaaaaaaact cccgcaattt cttatagaat acgttgaaaa ttaaatgtac    13140
gcgccaagat aagataacat atatctagat gcagtaatat acacagattc ccgcggacgt    13200
gggaaggaaa aaattagata acaaaatctg agtgatatgg aaattccgct gtatagctca    13260
tatctttccc tccaccgcgg tggtcgactt tcacatacgt tgcatacgtc gatatagata    13320
ataatgataa tgacagcagg attatcgtaa tacgtaatag ctgaaaatct caaaaatgtg    13380
tgggtcatta cgtaaataat gataggaatg ggattcttct attttttcctt tttccattct    13440 agcagccgtc gggaaaacgt ggcatcctct ctttcgggct caattggagt cacgctgccg    13500
tgagcatcct ctctttccat atctaacaac tgagcacgta accaatggaa aagcatgagc    13560
ttagcgttgc tccaaaaaag tattggatgg ttaataccat ttgtctgttc tcttctgact    13620
ttgactcctc aaaaaaaaaa atctacaatc aacagatcgc ttcaattacg ccctcacaaa    13680
aacttttttc cttcttcttc gcccacgtta aattttatcc ctcatgttgt ctaacggatt    13740
tctgcacttg atttattata aaagacaaa gacataaac ttctctatca atttcagtta    13800
ttgttcttcc ttgcgttatt cttctgttct tcttttttctt ttgtcatata taaccataac    13860
caagtaatac atattcaaac ttaagactcg agatggtcaa accaattata gctcccagta    13920
tccttgcttc tgacttcgcc aacttgggtt gcgaatgtca taggtcatc aacgccggcg    13980 cagattggtt acatatcgat gtcatggacg gccatttttgt tccaaacatt actctgggcc    14040
aaccaattgt tacctcccta cgtcgttctg tgccacgccc tggcgatgct agcaacacag    14100
aaaagaagcc cactgcgttc ttcgattgtc acatgatggt tgaaaatcct gaaaaatggg    14160
tcgacgattt tgctaaatgt ggtgctgacc aatttacgtt ccactacgag gccacacaag    14220 acccttttgca tttagttaag ttgattaagt ctaagggcat caaagctgca tgcgccatca    14280
```

```
aacctggtac ttctgttgac gttttatttg aactagctcc tcatttggat atggctcttg    14340
ttatgactgt ggaacctggg tttggaggcc aaaaattcat ggaagacatg atgccaaaag    14400
tggaaacttt gagagccaag ttcccccatt tgaatatcca agtcgatggt ggtttgggca    14460
aggagaccat cccgaaagcc gccaaagccg gtgccaacgt tattgtcgct ggtaccagtg    14520
ttttcactgc agctgacccg cacgatgtta tctccttcat gaaagaagaa gtctcgaagg    14580
aattgcgttc tagagatttg ctagattaga cgtctgttta agattacgg atatttaact     14640 tacttagaat aatgccattt ttttgagtta taataatcct acgttagtgt gagcgggatt    14700
taaactgtga ggaccttaat acattcagac acttctgcgg tatcacccta cttattccct    14760
tcgagattat atctaggaac ccatcaggtt ggtggaagat tacccgttct aagacttttc    14820
agcttcctct attgatgtta cacctggaca cccctttct ggcatccagt ttttaatctt     14880
cagtggcatg tgagattctc cgaaattaat taaagcaatc acacaattct ctcggatacc    14940
acctcggttg aaactgacag gtggtttgtt acgcatgcta atgcaaagga gcctatatac    15000
ctttggctcg gctgctgtaa cagggaatat aaagggcagc ataatttagg agtttagtga    15060
acttgcaaca tttactattt tcccttctta cgtaaatatt tttctttta attctaaatc      15120 aatcttttc aattttttgt tgtattctt tccttgctta aatctataac tacaaaaaac       15180
acatacataa actaaaacgt acgactagta tgtctgaacc agctcaaaag aaacaaaagg    15240
ttgctaacaa ctctctagaa caattgaaag cctccggcac tgtcgttgtt gccgacactg    15300
gtgatttcgg ctctattgcc aagtttcaac ctcaagactc cacaactaac ccatcattga    15360
tcttggctgc tgccaagcaa ccaacttacg ccaagttgat cgatgttgcc gtggaatacg    15420
gtaagaagca tggtaagacc accgaagaac aagtcgaaaa tgctgtggac agattgttag    15480
tcgaattcgg taaggagatc ttaaagattg ttccaggcag agtctccacc gaagttgatg    15540
ctagattgtc ttttgacact caagctacca ttgaaaaggc tagacatatc attaaattgt    15600
ttgaacaaga aggtgtctcc aaggaaagag tccttattaa aattgcttcc acttgggaag    15660
gtattcaagc tgccaaagaa ttggaagaaa aggacggtat ccactgtaat ttgactctat    15720
tattctcctt cgttcaagca gttgcctgtg ccgaggccca agttactttg atttccccat    15780
ttgttggtag aattctagac tggtacaaat ccagcactgg taaagattac aagggtgaag    15840
ccgacccagg tgttatttcc gtcaagaaaa tctacaacta ctacaagaag tacgttacaa    15900
agactattgt tatgggtgct tctttcagaa gcactgacga aatcaaaaac ttggctggtg    15960
ttgactatct aacaatttct ccagctttat tggacaagtt gatgaacagt actgaaacctt    16020 tcccaagagt tttggaccct gtctccgcta agaaggaagc cggcgacaag atttcttaca    16080
tcagcgacga atctaaattc agattcgact tgaatgaaga cgctatggcc actgaaaaat    16140
tgtccgaagg tatcagaaaa ttctctgccg atattgttac tctattcgac ttgattgaaa    16200
agaaagttac cgcttaagga agtatctcgg aaatattaat ttaggccatg tccttatgca    16260
cgtttctttt gatacttacg ggtacatgta cacaagtata tctatatata taaattaatg    16320
aaaatcccct atttatatat atgactttaa cgagacagaa cagtttttta ttttttatcc    16380
tatttgatga atgatacagt ttcg                                           16404

<210> SEQ ID NO 15
<211> LENGTH: 95
<212> TYPE: DNA
<213> ORGANISM: Artificial sequence
<220> FEATURE:
<223> OTHER INFORMATION: as a URA3 deletion scar in the genome -After
``` removal of the KanMX marker using the cre recombinase, a 95 bp
sequence consisting of a loxP site flanked by the primer binding
sites remained

<400> SEQUENCE: 15
gcattgcgga ttacgtattc taatgttcag ataacttcgt atagcataca ttatacgaag     60
ttatccagtg atgatacaac gagttagcca aggtg                                95

<210> SEQ ID NO 16
<211> LENGTH: 100
<212> TYPE: DNA
<213> ORGANISM: Saccharomyces cerevisiae

<400> SEQUENCE: 16
gtccataaag cttttcaatt catcttttt tttttttgttc tttttttga ttccggtttc      60 tttgaaattt ttttgattcg gtaatctccg agcagaagga                          100

<210> SEQ ID NO 17
<211> LENGTH: 100
<212> TYPE: DNA
<213> ORGANISM: Saccharomyces cerevisiae

<400> SEQUENCE: 17
aaaactgtat tataagtaaa tgcatgtata ctaaactcac aaattagagc ttcaatttaa     60
ttatatcagt tattacccgg gaatctcggt cgtaatgatt                          100

<210> SEQ ID NO 18
<211> LENGTH: 100
<212> TYPE: DNA
<213> ORGANISM: saccharomyces cerevisiae

<400> SEQUENCE: 18
attggcatta tcacataatg aattatacat tatataaagt aatgtgattt cttcgaagaa     60
tatactaaaa aatgagcagg caagataaac gaaggcaaag                          100

<210> SEQ ID NO 19
<211> LENGTH: 100
<212> TYPE: DNA
<213> ORGANISM: Saccharomyces cerevisiae

<400> SEQUENCE: 19
tagtgacacc gattatttaa agctgcagca tacgatatat atacatgtgt atatatgtat     60
acctatgaat gtcagtaagt atgtatacga acagtatgat                          100

<210> SEQ ID NO 20
<211> LENGTH: 6728
<212> TYPE: DNA
<213> ORGANISM: Artificial sequence
<220> FEATURE:
<223> OTHER INFORMATION: constructed vector

<400> SEQUENCE: 20
acatatttga atgtatttag aaaaataaac aaataggggt tccgcgcaca tttccccgaa     60
aagtgccacc tggtcctttt tcatcacgtg ctataaaaat aattataatt taaattttttt   120 aatataaata tataaattaa aaatagaaag taaaaaaaga aattaaagaa aaaatagttt   180
ttgttttccg aagatgtaaa agactctagg gggatcgcca acaaatacta ccttttatct    240
tgctcttcct gctctcaggt attaatgccg aattgtttca tcttgtctgt gtagaagacc    300
acacacgaaa atcctgtgat tttacatttt acttatcgtt aatcgaatgt atatctattt    360

```
aatctgcttt tcttgtctaa taaatatata tgtaaagtac gcttttgtt gaaattttt       420
aaacctttgt ttattttttt ttcttcattc cgtaactctt ctaccttctt tatttacttt    480
ctaaaatcca aatacaaaac ataaaaataa ataaacacag agtaaattcc caaattattc    540
catcattaaa agatacgagg cgcgtgtaag ttacaggcaa gcgatccgtc ctaagaaacc    600
attattatca tgacattaac ctataaaaat aggcgtatca cgaggccctt tcgtctcgcg    660
cgtttcggtg atgacggtga aaacctctga cacatgcagc tcccggagac ggtcacagct    720
tgtctgtaag cggatgccgg gagcagacaa gcccgtcagg gcgcgtcagc gcgtgttggc    780
gggtgtcggg gctggcttaa ctatgcggca tcagagcaga ttgtactgag agtgcaccat    840
aaattcccgt tttaagagct tggtgagcgc taggagtcac tgccaggtat cgtttgaaca    900
cggcattagt cagggaagtc ataacacagt cctttcccgc aatttctttt ttctattact    960
cttggcctcc tctagtacac tctatatttt tttatgcctc ggtaatgatt ttcattttt    1020
tttttcccct agcggatgac tctttttttt tcttagcgat tggcattatc acataatgaa   1080
ttatacatta tataaagtaa tgtgatttct tcgaagaata tactaaaaaa tgagcaggca   1140
agataaacga aggcaaagat gacagagcag aaagccctag taaagcgtat tacaaatgaa   1200
accaagattc agattgcgat ctctttaaag ggtggtcccc tagcgataga gcactcgatc   1260
ttcccagaaa aagaggcaga agcagtagca gaacaggcca cacaatcgca agtgattaac   1320
gtccacacag gtatagggtt tctggaccat atgatacatg ctctggccaa gcattccggc   1380
tggtcgctaa tcgttgagtg cattggtgac ttacacatag acgaccatca caccactgaa   1440
gactgcggga ttgctctcgg tcaagctttt aaagaggccc tactggcgcg tggagtaaaa   1500
aggtttggat caggatttgc gccttttggat gaggcacttt ccagagcggt ggtagatctt   1560
tcgaacaggc cgtacgcagt tgtcgaactt ggtttgcaaa gggagaaagt aggagatctc   1620
tcttgcgaga tgatcccgca ttttcttgaa agctttgcag aggctagcag aattaccctc   1680
cacgttgatt gtctgcgagg caagaatgat catcaccgta gtgagagtgc gttcaaggct   1740
cttgcggttg ccataagaga agccacctcg cccaatggta ccaacgatgt tccctccacc   1800
aaaggtgttc ttatgtagtg acaccgatta tttaaagctg cagcatacga tatatataca   1860
tgtgtatata tgtataccta tgaatgtcag taagtatgta tacgaacagt atgatactga   1920
agatgacaag gtaatgcatc attctatacg tgtcattctg aacgaggcgc gctttccttt   1980
tttcttttg cttttctt tttttctct tgaactcgac ggatctatgc ggtgtgaaat       2040
accgcacaga tgcgtaagga gaaaataccg catcaggaaa ttgtaaacgt taatatttg    2100
ttaaaattcg cgttaaattt ttgttaaatc agctcatttt ttaaccaata ggccgaaatc   2160
ggcaaaatcc cttataaatc aaaagaatag accgagatag ggttgagtgt tgttccagtt   2220
tggaacaaga gtccactatt aaagaacgtg gactccaacg tcaaagggcg aaaaaccgtc   2280
tatcagggcg atggcccact acgtgaacca tcacctaat caagttttt ggggtcgagg    2340
tgccgtaaag cactaaatcg gaaccctaaa gggagccccc gatttagagc ttgacgggga   2400
aagccggcga acgtggcgag aaaggaaggg aagaaagcga aaggagcggg cgctagggcg   2460
ctggcaagtg tagcggtcac gctgcgcgta accaccacac ccgccgcgct taatgcgccg   2520
ctacagggcg cgtcgcgcca ttcgccattc aggctgcgca actgttggga agggcgatcg   2580
gtgcgggcct cttcgctatt acgccagctg gcgaaagggg gatgtgctgc aaggcgatta   2640
agttgggtaa cgccagggtt ttcccagtca cgacgttgta aaacgacggc cagtgagcgc   2700
```

```
gcgtaatacg actcactata gggcgaattg ggtaccgggc cccccctcga ggtcgacggt   2760
atcgataagc ttgattagaa gccgccgagc gggcgacagc cctccgacgg aagactctcc   2820
tccgtgcgtc ctcgtcttca ccggtcgcgt tcctgaaacg cagatgtgcc tcgcgccgca   2880
ctgctccgaa caataaagat tctacaatac tagcttttat ggttatgaag aggaaaaatt   2940
ggcagtaacc tggccccaca aaccttcaaa ttaacgaatc aaattaacaa ccataggatg   3000
ataatgcgat tagtttttta gccttatttc tggggtaatt aatcagcgaa gcgatgattt   3060
ttgatctatt aacagatata taaatggaaa agctgcataa ccactttaac taatactttc   3120
aacattttca gtttgtatta cttcttattc aaatgtcata aaagtatcaa caaaaaattg   3180
ttaatatacc tctatacttt aacgtcaagg agaaaaatgt ccaatttact gcccgtacac   3240
caaaatttgc ctgcattacc ggtcgatgca acgagtgatg aggttcgcaa gaacctgatg   3300
gacatgttca gggatcgcca ggcgttttct gagcatacct ggaaaatgct tctgtccgtt   3360
tgccggtcgt gggcggcatg gtgcaagttg aataaccgga aatggtttcc cgcagaacct   3420
gaagatgttc gcgattatct tctatatctt caggcgcgcg gtctggcagt aaaaactatc   3480
cagcaacatt tgggccagct aaacatgctt catcgtcggt ccgggctgcc acgaccaagt   3540
gacagcaatg ctgtttcact ggttatgcgg cggatccgaa agaaaacgt tgatgccggt   3600 gaacgtgcaa acaggctct agcgttcgaa cgcactgatt tcgaccaggt tcgttcactc   3660
atggaaaata gcgatcgctg ccaggatata cgtaatctgg catttctggg gattgcttat   3720
aacaccctgt tacgtatagc cgaaattgcc aggatcaggg ttaaagatat ctcacgtact   3780
gacggtggga gaatgttaat ccatattggc agaacgaaaa cgctggttag caccgcaggt   3840
gtagagaagg cacttagcct gggggtaact aaactggtcg agcgatggat ttccgtctct   3900
ggtgtagctg atgatccgaa taactacctg ttttgccggg tcagaaaaaa tggtgttgcc   3960
gcgccatctg ccaccagcca gctatcaact cgcgccctgg aagggatttt tgaagcaact   4020
catcgattga tttacggcgc taaggatgac tctggtcaga gatacctggc ctggtctgga   4080
cacagtgccc gtgtcggagc cgcgcgagat atggcccgcg ctggagtttc aataccggag   4140
atcatgcaag ctggtggctg gaccaatgta aatattgtca tgaactatat ccgtaacctg   4200
gatagtgaaa caggggcaat ggtgcgcctg ctggaagatg gcgattagga gtaagcgaat   4260
ttcttatgat ttatgatttt tattattaaa taagttataa aaaaaataag tgtatacaaa   4320
ttttaaagtg actcttaggt tttaaaacga aaattcttat tcttgagtaa ctcttttcctg   4380 taggtcaggt tgctttctca ggtatagcat gaggtcgctc ttattgacca cacctctacc   4440
ggcatgccga gcaaatgcct gcaaatcgct ccccatttca cccaattgta gatatgctaa   4500
ctccagcaat gagttgatga atctcggtgt gtattttatg tcctcagagg acaacacctg   4560
tggtgttcta gagcggccgc caccgcggtg gagctccagc ttttgttccc tttagtgagg   4620
gttaattgcg cgcttggcgt aatcatggtc atagctgttt cctgtgtgaa attgttatcc   4680
gctcacaatt ccacacaaca taggagccgg aagcataaag tgtaaagcct ggggtgccta   4740
atgagtgagg taactcacat taattgcgtt gcgctcactg cccgctttcc agtcgggaaa   4800
cctgtcgtgc cagctgcatt aatgaatcgg ccaacgcgcg gggagaggcg gtttgcgtat   4860
tgggcgctct tccgcttcct cgctcactga ctcgctgcgc tcggtcgttc ggctgcggcg   4920
agcggtatca gctcactcaa aggcggtaat acggttatcc acagaatcag gggataacgc   4980
aggaaagaac atgtgagcaa aaggccagca aaaggccagg aaccgtaaaa aggccgcgtt   5040
gctggcgttt ttccataggc tccgcccccc tgacgagcat cacaaaaatc gacgctcaag   5100
```

```
tcagaggtgg cgaaacccga caggactata aagataccag gcgtttcccc ctggaagctc    5160
cctcgtgcgc tctcctgttc cgaccctgcc gcttaccgga tacctgtccg cctttctccc    5220
ttcgggaagc gtggcgcttt ctcatagctc acgctgtagg tatctcagtt cggtgtaggt    5280
cgttcgctcc aagctgggct gtgtgcacga acccccgtt cagcccgacc gctgcgcctt     5340
atccggtaac tatcgtcttg agtccaaccc ggtaagacac gacttatcgc cactggcagc    5400
agccactggt aacaggatta gcagagcgag gtatgtaggc ggtgctacag agttcttgaa    5460
gtggtggcct aactacggct acactagaag gacagtattt ggtatctgcg ctctgctgaa    5520
gccagttacc ttcggaaaaa gagttggtag ctcttgatcc ggcaaacaaa ccaccgctgg    5580
tagcggtggt ttttttgttt gcaagcagca gattacgcgc agaaaaaaag gatctcaaga    5640
agatcctttg atcttttcta cggggtctga cgctcagtgg aacgaaaact cacgttaagg    5700
gattttggtc atgagattat caaaaaggat cttcacctag atcctttaa attaaaaatg      5760
aagttttaaa tcaatctaaa gtatatatga gtaaacttgg tctgacagtt accaatgctt    5820
aatcagtgag gcacctatct cagcgatctg tctatttcgt tcatccatag ttgcctgact    5880
ccccgtcgtg tagataacta cgatacggga gggcttacca tctggcccca gtgctgcaat    5940
gataccgcga gacccacgct caccggctcc agatttatca gcaataaacc agccagccgg    6000
aagggccgag cgcagaagtg gtcctgcaac tttatccgcc tccatccagt ctattaattg     6060
ttgccgggaa gctagagtaa gtagttcgcc agttaatagt ttgcgcaacg ttgttgccat     6120
tgctacaggc atcgtggtgt cacgctcgtc gtttggtatg gcttcattca gctccggttc    6180
ccaacgatca aggcgagtta catgatcccc catgttgtgc aaaaaagcgg ttagctcctt    6240
cggtcctccg atcgttgtca gaagtaagtt ggccgcagtg ttatcactca tggttatggc    6300
agcactgcat aattctctta ctgtcatgcc atccgtaaga tgcttttctg tgactggtga    6360
gtactcaacc aagtcattct gagaatagtg tatgcggcga ccgagttgct cttgcccggc    6420
gtcaatacgg gataataccg cgccacatag cagaacttta aaagtgctca tcattggaaa    6480
acgttcttcg gggcgaaaac tctcaaggat cttaccgctg ttgagatcca gttcgatgta    6540
acccactcgt gcacccaact gatcttcagc atctttact ttcaccagcg tttctgggtg      6600
agcaaaaaca ggaaggcaaa atgccgcaaa aaagggaata agggcgacac ggaaatgttg    6660
aatactcata ctcttccttt ttcaatatta ttgaagcatt tatcagggtt attgtctcat    6720
gagcggat                                                             6728
```